(12) United States Patent
Hartney et al.

(10) Patent No.: US 9,994,901 B2
(45) Date of Patent: Jun. 12, 2018

(54) PRO-INFLAMMATORY MEDIATORS IN DIAGNOSIS AND TREATMENT OF CHRONIC OBSTRUCTIVE PULMONARY DISEASE

(71) Applicants: The Regents of the University of Colorado, Boulder, CO (US); National Jewish Health, Denver, CO (US)

(72) Inventors: John M. Hartney, Arvada, CO (US); Raul M. Torres, Denver, CO (US); Roberta Pelanda, Denver, CO (US)

(73) Assignees: NATIONAL JEWISH HEALTH, A NON-PROFIT ORGANIZATION, Denver, CO (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 233 days.

(21) Appl. No.: 14/391,484

(22) PCT Filed: Apr. 9, 2013

(86) PCT No.: PCT/US2013/035731
§ 371 (c)(1),
(2) Date: Oct. 9, 2014

(87) PCT Pub. No.: WO2014/011273
PCT Pub. Date: Jan. 16, 2014

(65) Prior Publication Data
US 2015/0051259 A1     Feb. 19, 2015

Related U.S. Application Data

(60) Provisional application No. 61/621,733, filed on Apr. 9, 2012.

(51) Int. Cl.
*A61K 31/5575*   (2006.01)
*G01N 33/68*     (2006.01)
*C12Q 1/68*      (2018.01)

(52) U.S. Cl.
CPC ........ *C12Q 1/6883* (2013.01); *A61K 31/5575* (2013.01); *G01N 33/6893* (2013.01); *C12Q 2600/106* (2013.01); *C12Q 2600/112* (2013.01); *G01N 2800/122* (2013.01); *G01N 2800/52* (2013.01)

(58) Field of Classification Search
None
See application file for complete search history.

(56) References Cited

U.S. PATENT DOCUMENTS 6,020,380 A * 2/2000 Killian ................. A61K 31/192
                                                    514/570
2006/0211026 A1  9/2006 Belloni et al.

OTHER PUBLICATIONS

Aldonyte, R. et al. Circulating monocytes from healthy individuals and COPD patients. Respiratory Research, 2003, vol. 4, p. 1-8.*
Goldbergova, P, et al. Rantes, MCP-1 chemokines and factors describing rheumatoid arthritis. Molecular Immunology, 2012, vol. 52, p. 273-278.*
Taylor, P.M., et al. Influenza virus-specific T cells lead to early interferon gamma in lungs of infected hosts: Devopment of a sensitive radioimmunoassay. J. Gen. Virol., 1989, vol. 70, p. 975-978.*
Barnes, "Mediators of Chronic Obstructive Pulmonary Disease," Pharmacol Rev., vol. 56, No. 4, pp. 515-548. Dec. 2004. entire document.
Hartney et al., "Thromboxane Receptor Signaling Is Required for Fibronectin-induced Matrix Metalloproteinase 9 Production by Human and Murine Macrophages and Is Attenuated by the Arhgef1 Molecule," J. Biol. Chem., vol. 286, pp. 44521-44531. Nov. 15, 2011.
De Fougerolles et al., "Global Expression Analysis of Extracellular Matrix-Integrin Interactions in Monocytes," Immunity, vol. 13, pp. 749-758. Dec. 2008. entire document.
Ishizuka et al., "Thromboxane A2 (TXA2) receptor blockade suppresses monocyte chemoattractant prtein-1 (MCP-1) expression by stimulated vascular endothelial cells," Clin. Exp. Immunol., vol. 120, p. 71-78. Apr. 2000. entire document.

* cited by examiner

*Primary Examiner* — Robert S Landsman
*Assistant Examiner* — Bruce D. Hissong
(74) *Attorney, Agent, or Firm* — William A. Ziehler; Shumaker, Loop & Kendrick, LLP

(57) ABSTRACT

Treatment and diagnostic methods are provided for pulmonary disease, including chronic obstructive pulmonary disease. Various pro-inflammatory mediators are elevated in a model of COPD that can be used predict the presence of COPD and/or subtypes of COPD in human patients. Profiles of these mediators can also predict the responsiveness of some patients to certain therapies, including thromboxane receptor antagonist treatment. Methods are provided for diagnosing a subject as a pulmonary disease candidate that include determining leukocyte expression in the subject of at least one pro-inflammatory mediator and identifying the subject as a pulmonary disease candidate when leukocyte expression in the subject of the pro-inflammatory mediator is increased compared to leukocyte expression of the pro-inflammatory mediator in a healthy individual. The pulmonary disease candidate can also be treated by administering a therapeutically effective amount of a thromboxane receptor antagonist.

9 Claims, 25 Drawing Sheets

□ = healthy plastic (n=3)   ■ = COPD plastic (n=9)   □ = healthy FN (n=3)   ▨ = COPD FN (n=9)

GM-CSF

IFN-γ

IL-10

IL-12 p70

PRO-INFLAMMATORY MEDIATORS IN DIAGNOSIS AND TREATMENT OF CHRONIC OBSTRUCTIVE PULMONARY DISEASE

CROSS-REFERENCE TO RELATED APPLICATIONS

This application claims the benefit of U.S. Provisional Application No. 61/621,733, filed on Apr. 9, 2012. The entire disclosure of the above application is incorporated herein by reference.

GOVERNMENT RIGHTS

This invention was made with U.S. government support under grant number AI1007045 awarded by the National Institutes of Health. The U.S. government has certain rights in the invention.

FIELD

The present technology relates to various diagnoses and treatments for pulmonary disease, such as chronic obstructive pulmonary disease, including the use of pro-inflammatory mediators to identify disease candidates for treatment.

BACKGROUND

This section provides background information related to the present disclosure which is not necessarily prior art.

Inflammation is a host response to infection important for pathogen elimination but which also leads to tissue injury that must be repaired. Accordingly, the inflammation response must be tightly regulated as aberrant or excessive inflammation can also result in tissue injury caused by responding leukocytes. Moreover, prolonged pro-inflammatory stimulation or an inability to resolve acute inflammation can contribute to the pathogenesis of a number of diseases that include chronic obstructive pulmonary disease (COPD), asthma, cancer, atherosclerosis, and autoimmunity. With regard to COPD, continual stimulation through repeated cigarette smoke exposure leads to chronic inflammation that is perpetuated even years after cigarette smoke exposure has terminated. Thus, defining the molecular pathways that lead to inflammation, and the identification of possible points of intervention in these pathways are warranted.

The acute inflammatory response to pathogens initiates with tissue injury and/or exposure of pathogen-derived ligands that engage Toll-like receptors expressed on resident tissue macrophages. Macrophages are innate immune cells that reside in diverse tissues and provide sentinel responses against pathogens or noxious substances by the production of pro-inflammatory mediators, such as vasoactive lipids, cytokines, and chemokines. An immediate consequence of this tissue macrophage response is the recruitment of neutrophils that within hours release their granule contents at the site of infection in an attempt to eradicate or neutralize pathogens. However, this response can also lead to local tissue injury. Recruited macrophages, differentiated from newly arriving monocytes, clear remaining pathogens and short-lived apoptotic neutrophils via phagocytosis and begin tissue repair through the production of angiogenic factors and proteolytic tissue enzymes, such as matrix metalloproteases (MMPs). Under normal circumstances, the acute inflammatory response to pathogen exposure is resolved within days.

In tissues, macrophages use integrins to adhere to integrin ligands found in extracellular matrix (ECM) proteins (e.g. collagen and fibronectin) or expressed on the cell surface of other cells (e.g. ICAM and VCAM). The adhesion of myeloid cell to ECM integrin ligands has repeatedly been shown to promote production of many pro-inflammatory mediators such as prostaglandins, inflammatory cytokines, chemokines, and multiple MMPs. Although the production of prostaglandins is known to be dependent on cyclooxygenase activity, the integrin signaling pathways macrophages use to produce other pro-inflammatory mediators are not well understood, although mitogen-activated protein kinases, Src family, and Pyk2 nonreceptor tyrosine kinases are implicated in integrin signaling. Work from our laboratory has found that macrophage adhesion to fibronectin via the α5β1 integrin in vitro leads to MMP-9 production and is normally inhibited by the Arhgef1 intracellular signaling molecule.

Arhgef1 (Lsc/p115RhoGEF) is an intracellular signaling molecule with expression predominantly restricted to hematopoietic cells. Arhgef1 is biochemically and functionally characterized as both a regulator of G-protein signaling (RGS) and Rho guanine nucleotide exchange factor. RGS proteins act as GTPase-activating proteins for GTP-bound Gα subunits of heterotrimeric G-proteins. Arhgef1 specifically accelerates the inherent GTPase activity of $G\alpha_{12/13}$ subunits, thereby terminating signaling from GPCRs that associate with $G\alpha_{12/13}$-containing heterotrimeric G-proteins. Arhgef1 also contains a tandem Dbl and pleckstrin homology domain that functions as Rho guanine nucleotide exchange factor specific for RhoA. RhoA participates in a number of cell biological processes including regulating cytoskeletal organization, integrin adhesion, and integrin signaling. We have shown that in B-lymphocytes, Arhgef1 is required for resolving integrin adhesion, and analyses of Arhgef1-deficient mouse mutants have further demonstrated a requirement for Arhgef1 in leukocyte migration and adhesion, consistent with the reported role for Arhgef1 in fibroblast adhesion to fibronectin.

SUMMARY

The present technology includes various embodiments of systems, processes, methods, articles of manufacture, and compositions that relate to pulmonary disease treatments and diagnostics. The diagnosis and treatment of pulmonary diseases using the present technology is based in part on the discovery that thromboxane receptor signaling is required for fibronectin-induced matrix metalloproteinase 9 (MMP-9) production by human and murine macrophages and that the signaling is attenuated by the Arhgef1 molecule. In particular, Arhgef1$^{-/-}$ macrophages exhibit exaggerated matrix metalloproteinase-9 (MMP-9) production when cultured on fibronectin. Thromboxane is produced by myeloid cells when cultured on fibronectin, and treatment with thromboxane receptor (TP) antagonist ablates MMP-9 production. Accordingly, TP signaling is required for MMP-9 production by myeloid cells cultured on fibronectin. TP antagonists can therefore be therapeutic for reducing myeloid MMP-9 production in inflammatory diseases, including pulmonary diseases such as COPD. The present technology is further based on the discovery that expression of various pro-inflammatory mediators can be indicative of pulmonary diseases such as COPD.

Embodiments include methods of diagnosing a subject as a pulmonary disease candidate where leukocyte expression of at least one pro-inflammatory mediator is determined in the subject. The subject is identified as a pulmonary disease candidate when leukocyte expression in the subject of the pro-inflammatory mediator is increased compared to leukocyte expression of the pro-inflammatory mediator in a healthy individual. Pro-inflammatory mediators are molecules, signaling molecules, and second messengers, that correlate with inflammation and/or are indicative of an inflammatory response.

Certain embodiments include a method of diagnosing a subject as a pulmonary disease candidate and treating the pulmonary disease candidate where leukocyte expression in the subject of at least one pro-inflammatory mediator is determined. The subject is identified as a pulmonary disease candidate when leukocyte expression in the subject of the pro-inflammatory mediator is increased compared to leukocyte expression of the pro-inflammatory mediator in a healthy individual. The pulmonary disease candidate is treated by administering a therapeutically effective amount of a thromboxane receptor antagonist.

Further embodiments include a method of selecting a candidate compound for treating a pulmonary disease in a subject where a leukocyte comprising a thromboxane receptor is exposed to fibronectin and a compound. Whether the compound inhibits leukocyte expression of at least one pro-inflammatory mediator is determined. The compound is selected as a candidate compound for treating the pulmonary disease when leukocyte expression of the pro-inflammatory mediator is decreased compared to leukocyte expression of the pro-inflammatory mediator in an absence of the compound.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except in the examples, or where otherwise expressly indicated, all numerical quantities in this description indicating amounts of material or conditions of reaction and/or use are to be understood as modified by the word "about" in describing the broadest scope of the technology.

The present technology relates to innate lung immunity in health and pulmonary disease, including chronic obstructive pulmonary disease (COPD). Leukocytes are present in the lungs of healthy individuals and are necessary for the innate and adaptive immune response against potentially harmful foreign antigens that are inhaled on a constant basis. For antigenic challenges not cleared through mechanical expulsion or bactericidal agents, initial immune protection is provided by innate immunity and orchestrated by alveolar macrophages (AMs). Pathogens not eliminated by the innate immune response are subsequently met with the humoral and cellular arms of the adaptive immune response. Under normal circumstances, eradication of the inflammatory stimulus leads to resolution of inflammation and repair of the lung tissue. However, in the face of chronic stimulation, tissue damage often ensues and is true of COPD where chronic stimulation is provided not only by long-term cigarette smoking, but also occupational dust and chemical exposure as well as biomass cooking and heating.

Figure 1:
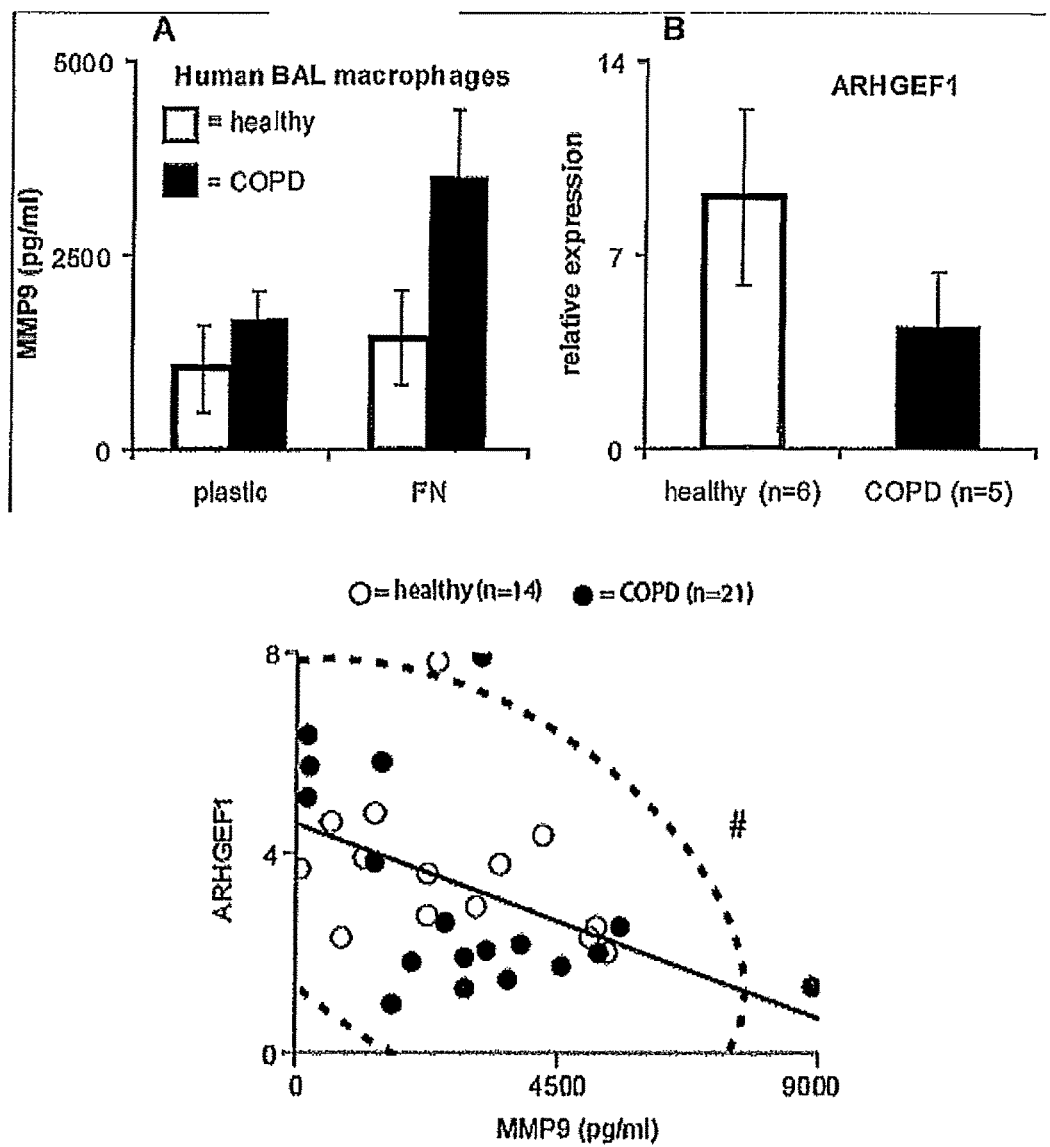
FIG. 1, Panel A graphically depicts MMP-9 concentrations measured for healthy and COPD human BAL macrophages cultured on plastic and fibronectin. Panel B graphically depicts the relative expression of ARHGEF1 in healthy and COPD subjects. Panel C graphically depicts the correlation between human PB healthy and COPD subjects. ARHGEF1 expression negatively correlates with MMP-9 production by monocytes cultured on fibronectin. Relative ARHGEF1 expression as measured by RT-PCR is shown on the y axis. ARHGEF1 expression was normalized to GAPDH expression and displayed relative to the lowest expressing individual. MMP-9 production was measured in conditioned media by ELISA and is shown on the x axis. Shown are the results from monocytes obtained from healthy individuals (open circles n=14) and patients with COPD (solid circles, n=21). A Pearson product moment correlation analysis was performed and a correlation coefficient of −0.4678 was obtained with a p=0.0069 between ARHGEF1 expression and MMP-9 production. The dotted line denotes bivariate normal ellipse for 95% of the values. The solid line represent the linear fit.
Figure 2A:
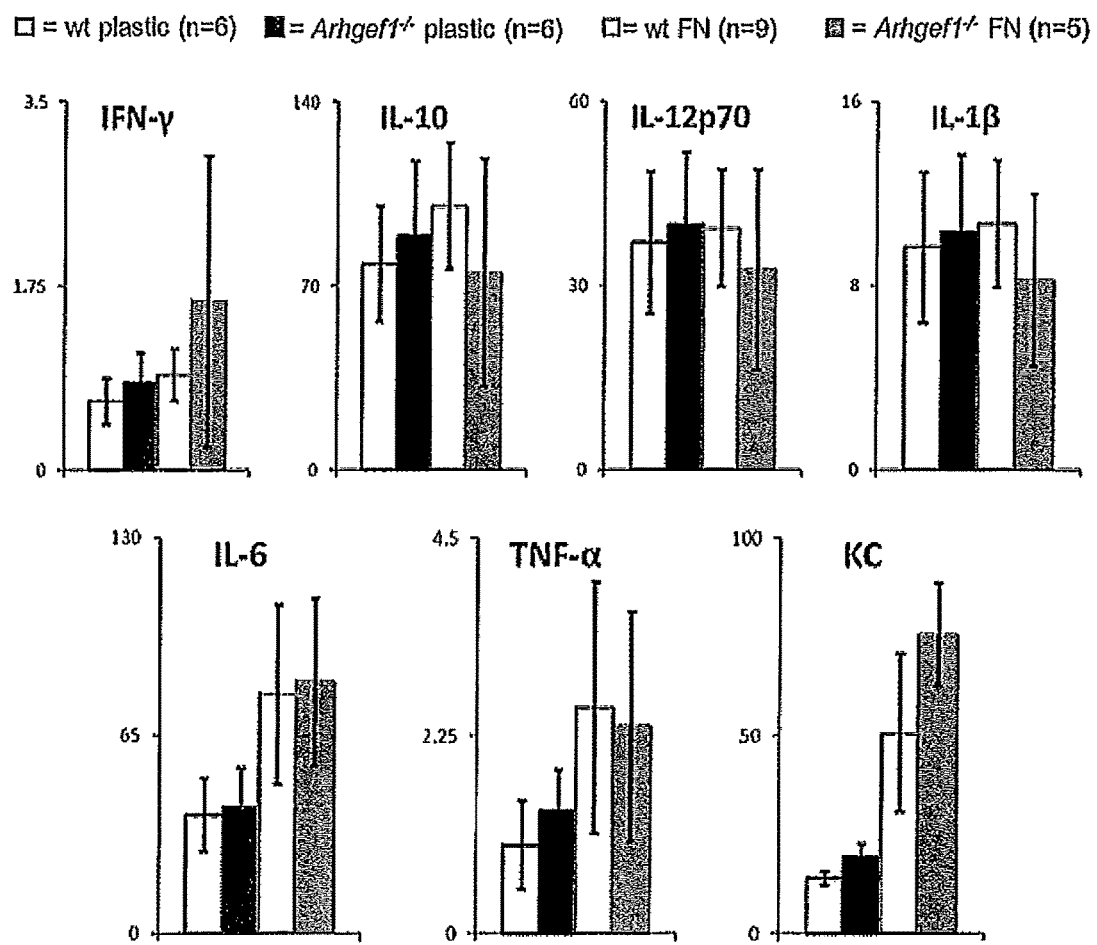
FIG. 2, Panel A graphically depicts concentrations of several pro-inflammatory mediators in conditioned media from resident murine peritoneal macrophages. Panels B, C, D, E, and F graphically depict concentrations of several pro-inflammatory mediators in conditioned media from human peripheral blood monocytes from healthy subjects (n=3) and patients with COPD (n=9) cultured on either plastic or fibronectin.
Figure 2B:
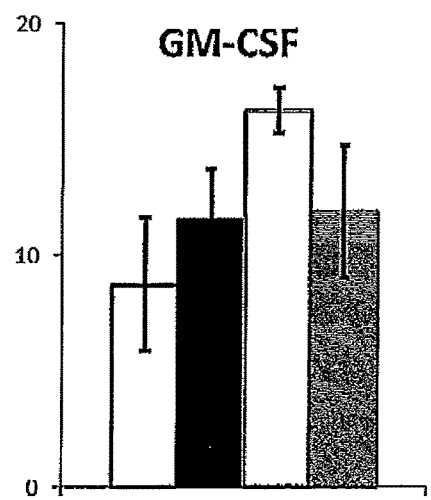
Figure 2B:
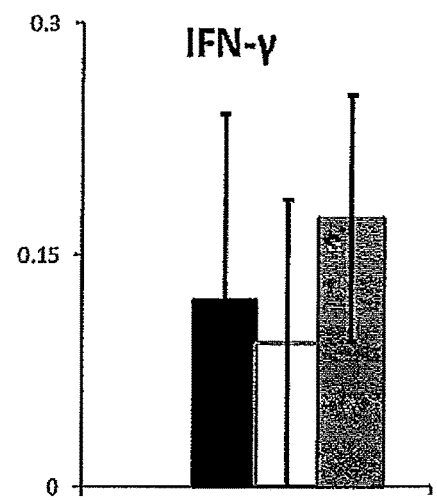
Figure 2B:
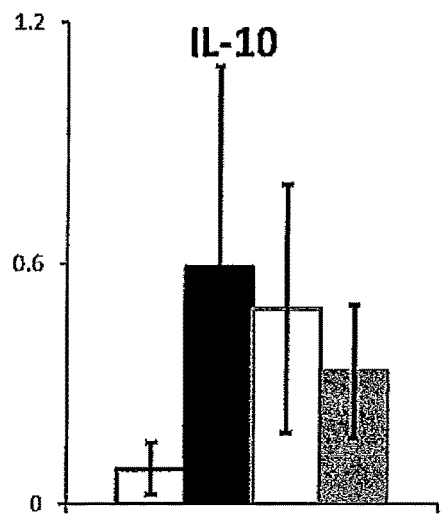
Figure 2B:
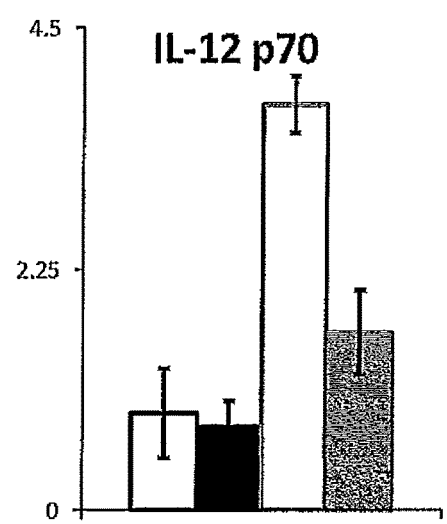
Figure 2C:
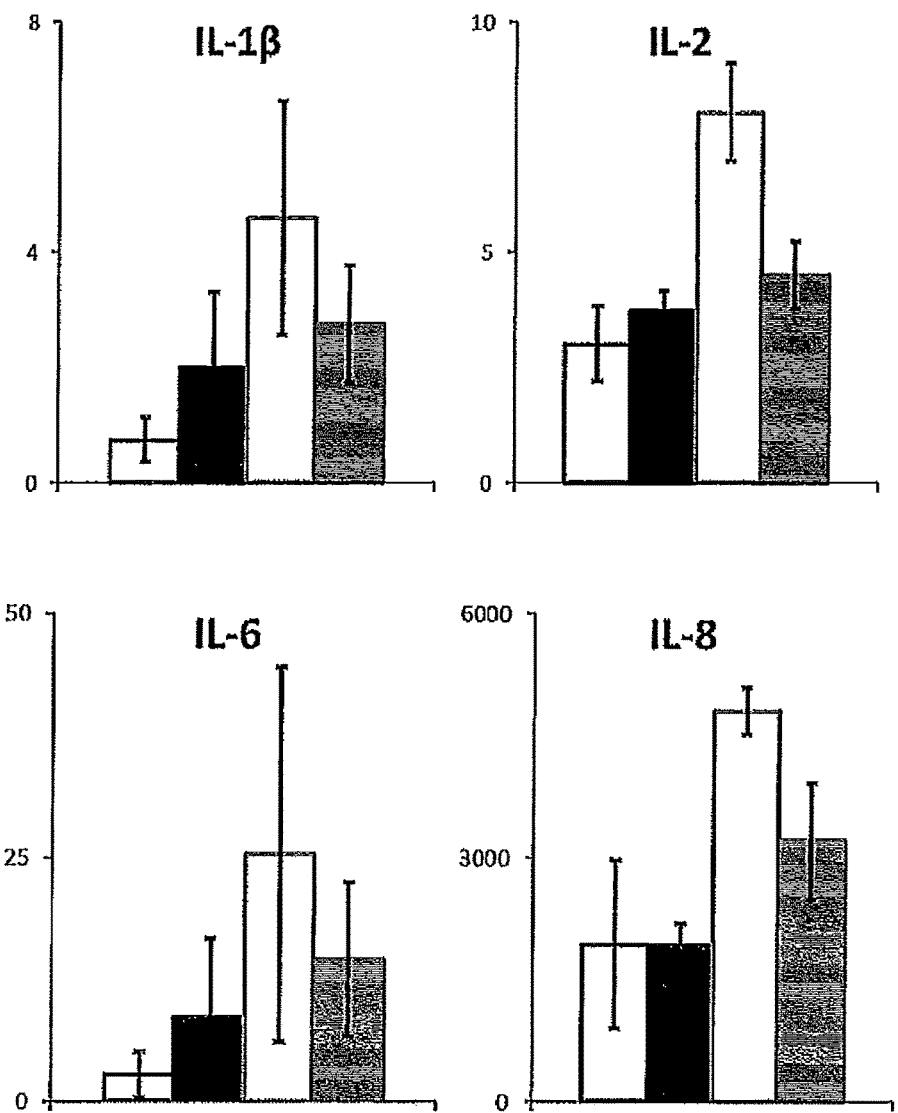
Figure 2D:
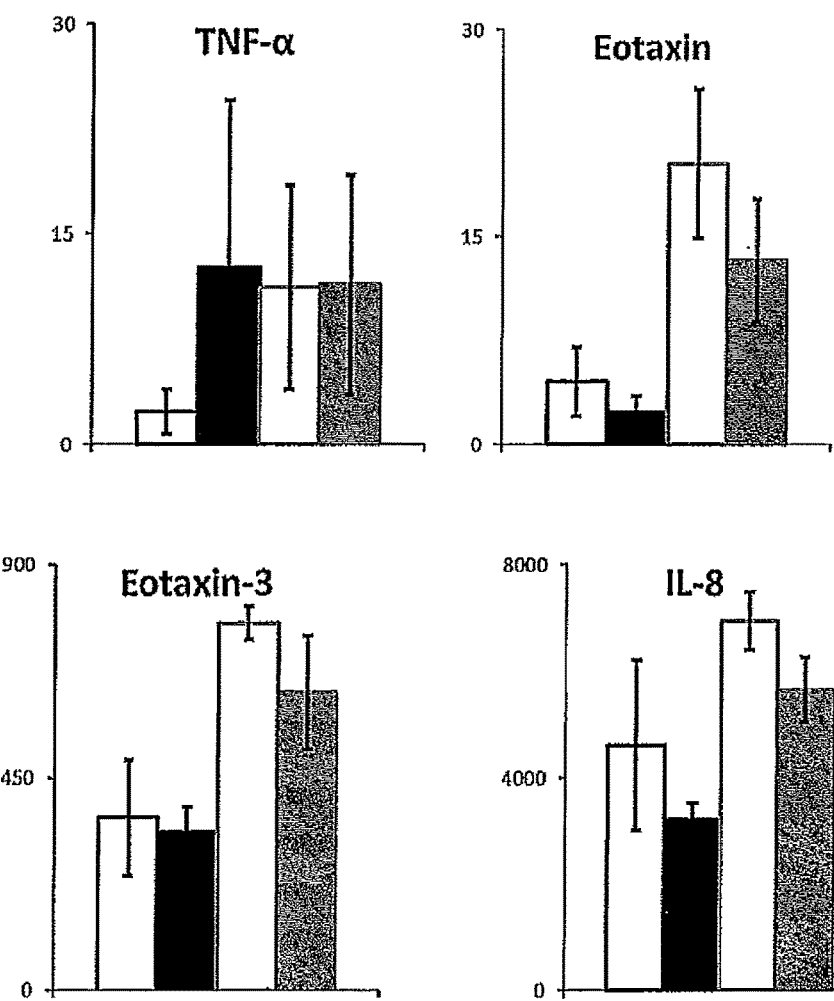
Figure 2E:
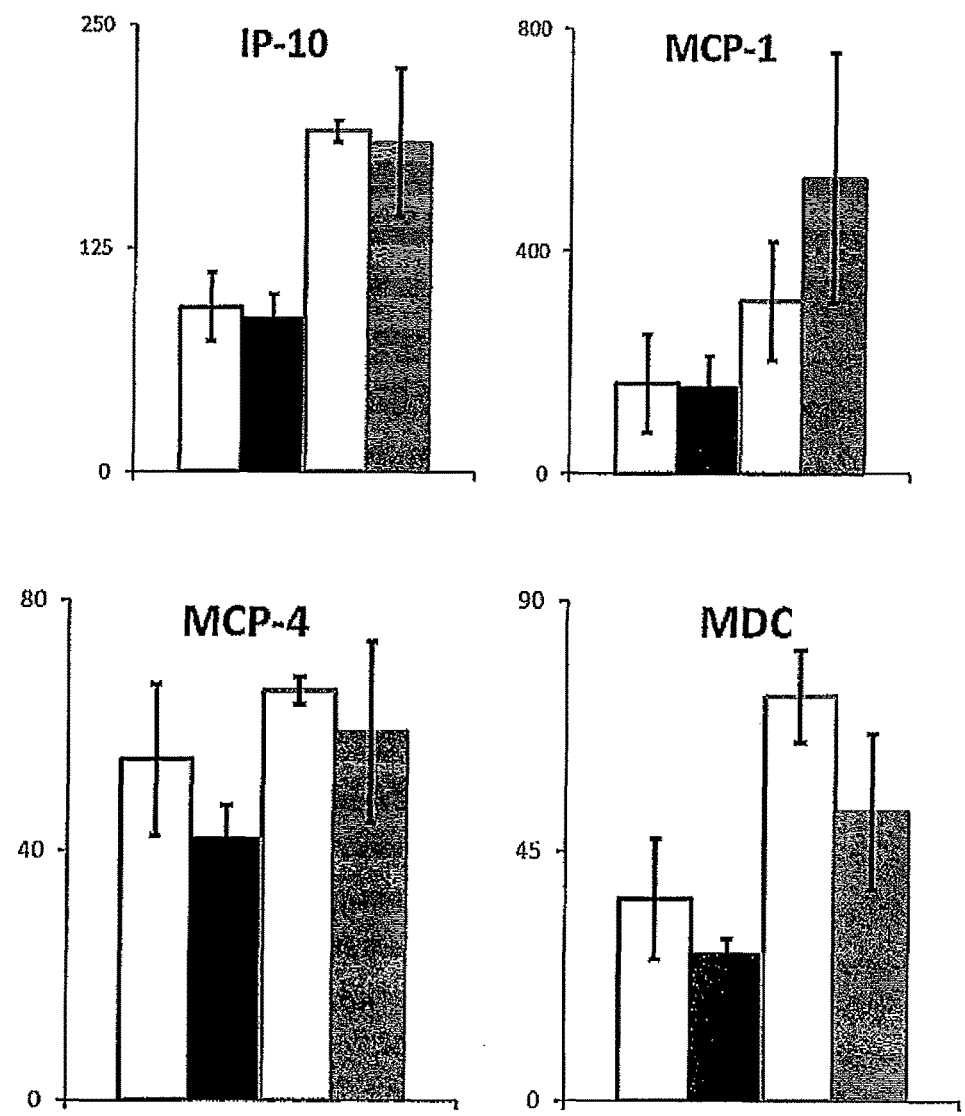
Figure 2F:
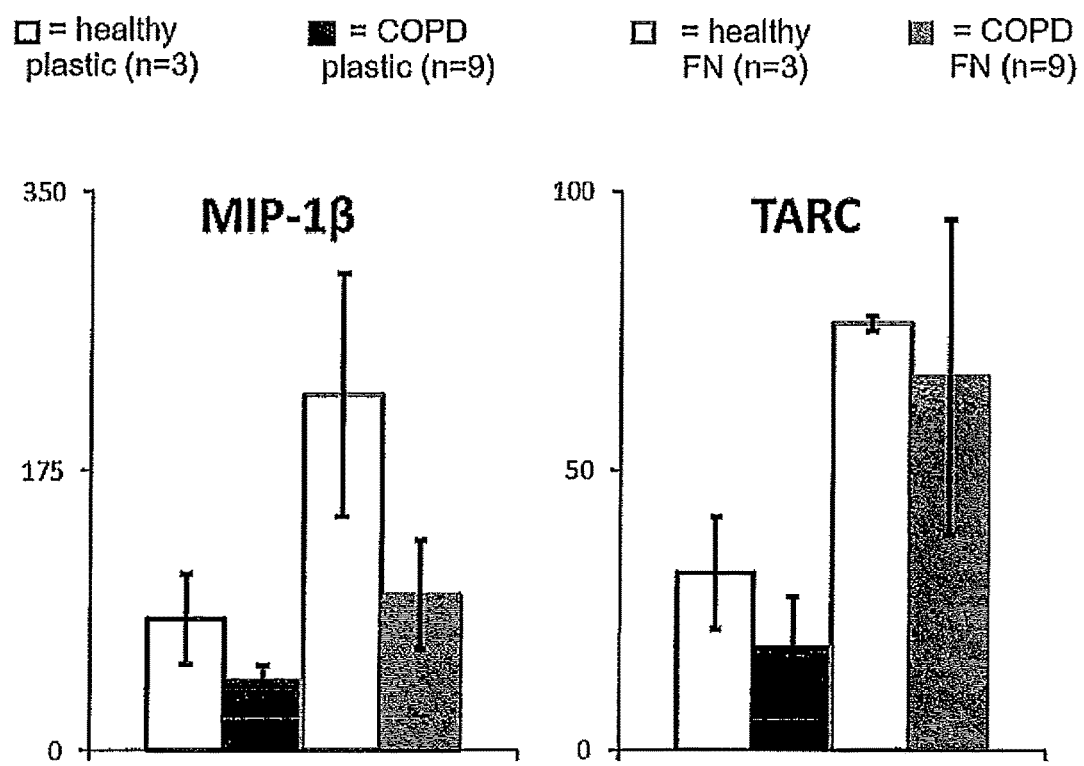

COPD is a heterogeneous disease that is diagnosed clinically and organized into progressive stages delineated by degree of airflow obstruction. Two somewhat independent pathologies lead to COPD: loss of parenchymal lung tissue, or emphysema, which affects the elastic recoil of the lungs, and a narrowing of the conducting airways and/or mucus hypersecretion, often referred to as obstructive bronchiolitis or small airways disease. The present inventors have shown in a mouse model that deficiency in leukocyte expression of Arhgef1, an intracellular signaling molecule, results in chronic inflammation in lung airspace and tissue, heightened matrix metalloproteinase (MMP) expression and activity, alveolar wall destruction (emphysema) and impaired lung function as indicated by reduced elastic recoil (FIG. 1). Interestingly, the present inventors have also found that leukocytes from individuals with COPD express significantly reduced levels of Arhgef1 protein compared with healthy individuals. These findings identify an association between Arhgef1, inflammation, and parenchymal tissue damage, thereby providing insight into the molecular nature of COPD lung pathology.

Macrophages provide various functions in health and in chronic obstructive pulmonary disease. Macrophages act as a sentinel in alerting lung innate and adaptive immune responses through interaction with alveolar epithelial cells. In response to local inflammatory mediators produced by epithelial cells, AMs clear or neutralize potential harmful insults by migrating along the alveolar epithelium, and facilitated by AM integrins, interacting with respective integrin ligands produced by epithelial cells. Indeed, in response to inflammatory stimuli or injury, epithelial cells are induced to express integrin ligands such as the extracelluar matrix component fibronectin. However, AMs have also been directly associated with lung tissue destruction in smokers and severity of COPD correlates with increased presence of these cells in addition to neutrophils and lymphocytes. It is believed that the subsequent response of AMs to these inflammatory mediators and integrin ligands expressed by these alveolar epithelial cells varies across individuals, Given that only a proportion of those chronically exposed to cigarette smoke develop emphysema, it is also believed that individuals whose macrophages exhibit exaggerated responses to these inflammatory mediators are predisposed for developing COPD.

An imbalance in protease/anti-protease levels leads to lung tissue destruction. The notion of an imbalance of proteases/anti-proteases in emphysema emerged with the identification that individuals with genetic mutations in the SERPINA1 gene encoding α-1 antitrypsin are predisposed to the development of this disease. Since then an imbalance in the levels of several other proteases and anti-proteases in the pulmonary compartment have been associated with human lung pathology, including MMP-2, MMP-9, MMP-12 and TIMP-1, and genetic associations with COPD have been implicated for MMP-9 and MMP-12. Macrophages are known to express each of these MMPs and AMs from COPD patients express exaggerated levels of several of these proteases. Of note, MMP-9 has repeatedly been shown to be elevated in AMs, lavage fluid, sputum, and serum from COPD individuals particularly implicating MMP-9 in COPD pathophysiology. Further evidence supporting a protease imbalance as an etiological basis of lung tissue destruction is derived from mouse models whose macrophages either over-express MMP-9 or are deficient in MMP12 and that promote or are refractory to the development of airspace enlargement, respectively. Together, these data indicate that a protease/anti-protease imbalance promotes the development of lung pathophysiology. Of the pulmonary proteases, an increased presence of MMP-9 is found in the lungs of emphysematous individuals where it has also been localized to the alveolar wall and site of tissue damage in emphysema and the present inventors have found that Arhgef1 acts to normally limit MMP-9 production. Thus, a better understanding of how alveolar macrophages produce MMP-9 and avenues to therapeutically interfere with the production of this MMP is warranted.

A new signaling pathway for, and regulation of, MMP production by pulmonary leukocytes is shown. An imbalance between protease and anti-protease activity is an established etiological basis for emphysema and MMPs are predominant pulmonary proteases that have also been implicated in lung pathology. Thus, identifying signaling pathways by which MMPs are generated within the lung is of fundamental importance. The present inventors have found a previously uncharacterized signaling pathway used by macrophages to generate MMP-9 and that is negatively-regulated by Arhgef1. Because Arhgef1 has been shown to inhibit G-protein coupled receptor (GPCR) signaling, it is believed that within an inflammatory setting, signaling via a GPCR is a key component of MMP-9 production leading to lung parenchymal tissue damage. Experiments by the present inventors show this GPCR is the thromboxane receptor expressed by pulmonary macrophages.

Establishment that an ARHGEF1 genetic signature is associated with Arhgef1 expression or MMP-9 production. Experiments by the present inventors have shown that ARHGEF1 expression is genetically determined. In some embodiments, methods can be used as prognostic and/or diagnostic tests for COPD, a disease currently diagnosed by lung function testing and computer tomography. Additional objects, advantages, and novel features of the technology will become apparent to those skilled in the art upon examination of the following examples thereof, which are not intended to be limiting.

Stimulation of macrophages or monocytes by fibronectin can identify COPD patients whose leukocytes exhibit increased production of pro-inflammatory mediators via reduced ARHGEF1 expression. These patients are hence amenable to thromboxane receptor inhibition therapy. In particular, profiles of one or more pro-inflammatory mediators can be used to predict COPD patient subtypes and responsiveness to therapy. The mouse model of COPD, as described herein, exhibits a particular profile of pro-inflammatory mediators in the lung. Culture of murine macrophages on fibronectin induces a similar pattern of pro-inflammatory mediators. We have conducted a series of experiments with alveolar macrophages and peripheral blood monocytes from healthy subjects and patients with COPD. A survey of these pro-inflammatory mediators shows that a similar induction pattern for these mediators occurs in patients with COPD. Dose response curves were also determined for in vitro responses to a thromboxane receptor antagonist.

As demonstrated herein, loss of Arhgef1 in murine leukocytes leads to spontaneous pulmonary inflammation and pathology similar to COPD in humans. Additionally we have determined that Arhgef1-deficent macrophages exhibit exaggerated thromboxane receptor signaling. The consequence of this exaggerated signaling is elevated production of pro-inflammatory mediators by Arhgef1-deficient macrophages when cultured on fibronectin, which is dependent on thromboxane receptor signaling both in vitro and in vivo.

The experiments described herein establish that various pro-inflammatory mediators are elevated in myeloid cells cultured on fibronectin from COPD patients compared to healthy individuals. These experiments include evaluation of the production of pro-inflammatory mediators in conditioned media from cells obtained from subjects who participated in the COPDGene study. A state-of-the-art multiplex ELISA based system was also used which allows quantitation of up to 9 mediators simultaneously in a 96 well format.

Macrophages have long been postulated to be one of the critical mediators for the development of COPD. The evidence supporting this includes the observation of elevated numbers of macrophages in both the bronchoalveolar lavage and lung tissue of patients with COPD as well as the elevated expression of pro-inflammatory mediators including MMP-9, MMP12, MCP-1, TNF-$\alpha$, IL-$\beta$. Given that only a proportion of individuals who smoke go on to develop COPD, it have been suggested that intrinsic factors influencing macrophage activation may contribute to an individual's susceptibility to develop COPD.

Prostanoids are a family of lipid mediators generated via arachidonic acid metabolism by cyclooxygenases and prostaglandin synthases. Over 15 years ago an association between prostanoids and COPD was initially established with the identification that COPD patients have elevated levels of thromboxane metabolites in urine. More recently investigators have found elevated levels of COX2, the inducible cyclooxygenase in both lung tissue and alveolar macrophages from COPD patients. Of note, a polymorphism which has been shown to diminish promoter activity of the COX2 gene was found to be more common in healthy smokers than patients with COPD. Evidence for a causative role of cyclooxygenase activity comes a recent animal study of cigarette smoke exposure which reported that treatment with a cyclooxygenase inhibitor attenuates pulmonary inflammation and pathology.

Arhgef1 is an intracellular signaling molecule which has been shown specifically to modulate signaling from G$\alpha$12/13 coupled receptors. Culturing of macrophages on fibronectin reveals an exaggerated production of MMP-9 by Arhgef1-deficient cells compared to wild type cells. We have identified that thromboxane receptor signaling is required for fibronectin induced MMP-9 expression in wild type and Arhgef1-deficient cells. Treatment of Arhgef1-deficient mice with a thromboxane receptor antagonist results in a consistent and reproducible reduction in MMP-9 expression and activity in the pulmonary compartment. A more detailed analysis of the lungs of Arhgef1-deficient mice has revealed elevated levels of multiple pro-inflammatory mediators including: IFN-$\gamma$, MCP-1, Egr-1, IL-6, and iNOS as measured by qPCR. Importantly treatment with a thromboxane receptor antagonist decreased expression of all of these mediators in the Arhgef1-deficient lungs. These findings were unexpected.

Our experiments with murine macrophages have identified that thromboxane receptor signaling is negatively regulated by Arhgef1 and is required for fibronectin induced production of MMP-9. Based on these results, we believe that macrophages from COPD patients would produce elevated levels of MMP-9 when cultured on fibronectin when compared to cells from healthy individuals. When we performed these experiments, we also collected RNA from our cultured cells to evaluate ARHGEF1 expression. Both BAL cells and peripheral blood monocytes from COPD patients displayed elevated MMP-9 production compared to healthy samples (FIG. 1A and data not shown). Not only do cells from COPD patients expressed diminished levels of ARHGEF1, but when we compare ARHGEF1 expression to MMP-9 production in samples where we measured both parameters, we find a statistically significant negative correlation between ARHGEF1 expression and MMP-9 production (FIG. 1C). Consistent with our murine experiments, we find that treatment of human cells with a thromboxane receptor antagonist attenuates the fibronectin induced production of MMP-9.

It was ascertained that various pro-inflammatory mediators are elevated in myeloid cells cultured on fibronectin from COPD patients compared to healthy individuals. This was done in view of experiments that demonstrate the ability of fibronectin to induce production of MMP-9 in both BAL macrophages and peripheral blood monocytes (FIG. 1). Based on the observation that multiple pro-inflammatory mediators are elevated in the lungs of patients with COPD and Arhgef1-deficient animals, we determined whether fibronectin would induce the production of other inflammatory mediators as well. To examine this, we employed a multiplex ELISA based technology (Meso Scale Discovery, Gaithersburg, Md. USA) to quantitate up to 9 independent secreted mediators per well in a 96 well format. Experiments were performed using both murine and human samples. For the murine experiments, we collected the conditioned media from resident peritoneal macrophages and utilized a pro-inflammatory 7-plex assay (see FIG. 2A). For the human studies, we collected conditioned media from peripheral blood monocytes of 3 healthy individuals and 9 with COPD. Nine-plex assays for human pro-inflammatory mediators and chemokines were used (see FIG. 2B-F). In both species, we have been able to consistently detect increases in various pro-inflammatory mediators when the cells are cultured on fibronectin (FIGS. 2A-F).

We have aliquots of conditioned media from peripheral blood monocytes cultured on either plastic, fibronectin, or fibronectin and a thromboxane receptor antagonist from over 30 individual subjects. Seventeen of these subjects have been clinically diagnosed with COPD and all of the subjects have participated in the COPDgene study, as described by Regan, E. A., Hokanson, J. E., Murphy, J. R., Make, B., Lynch, D. A., Beaty, T. H., Curran☐Everett, D., Silverman, E. K., and Crapo, J. D. (2010) *Copd* 7(1), 32☐43. Briefly, COPDGene is a large multicenter study which enrolled over 10,000 participants in order to investigate the genetic factors which may contribute to the development of COPD. In addition we have performed parallel studies with BAL cells from 13 subjects, 6 of which also participated in COPDgene as well. The production of pro-inflammatory mediators in these samples can be evaluated using a pro-inflammatory 9-plex ELISA kit which will simultaneously measure GM-CSF, IFN-γ, IL-1β, IL-10, IL-12p70, IL-2, IL-6, IL-8 and TNF-α.

Figure 3:
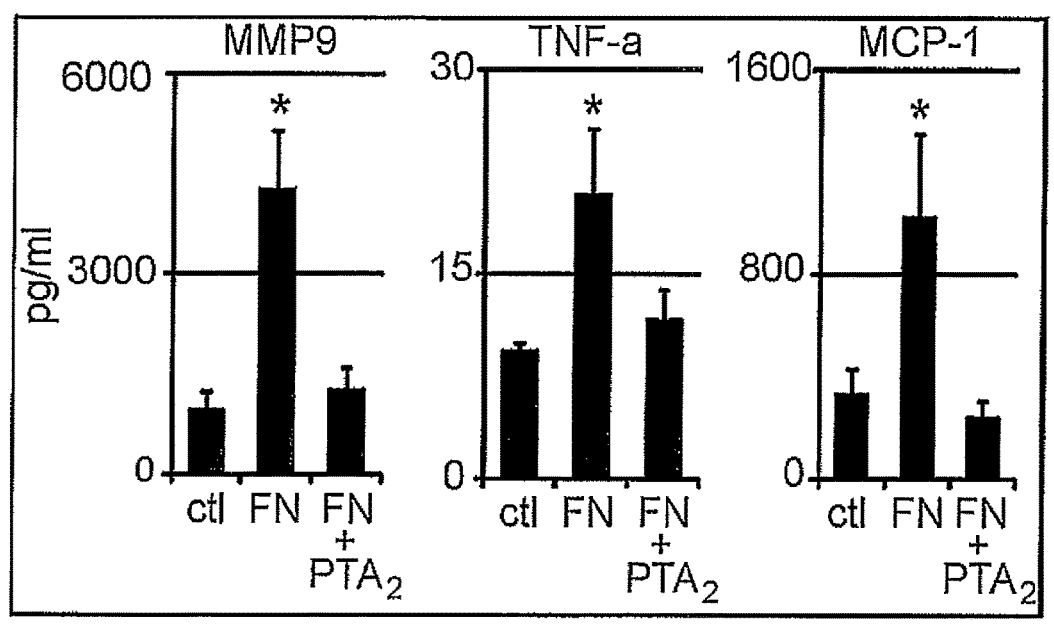
FIG. 3. FN induced MCP-1 and TNF- are dependent on TP signaling in human PB monocytes. Fibronectin (FN) induces pro-inflammatory mediator in human PB monocytes. Monocytes (n=6) were cultured on plastic (ctl) or fibronectin (FN) for 48 hrs. Pinane thromboxane $A_2$ ($PTA_2$), a thromboxane receptor antagonist, was added to some FN cultures. Conditioned media was analyzed for indicated mediators by ELISA. *P<0.05 Students two tailed t-test compared to plastic.

From these experiments, we have demonstrated that human myeloid cells use an autocrine thromboxane signaling pathway to promote inflammation that is suppressed by thromboxane receptor antagonism. In particular, murine macrophages promote inflammation via a signaling pathway that depends on thromboxane receptor signaling and that is repressed by ARHGEF1. Monocytes from a healthy individual similarly promote inflammation, as indicated by MMP-9, TNFα and MCP-1 production, and this is inhibited by a (commercially available research grade) thromboxane receptor antagonist (FIG. 3). This suggests human monocytes employ a similar thromboxane receptor autocrine signaling pathway to promote inflammation. In such experiments, we can demonstrate the significance of this finding by evaluating monocytes and alveolar macrophages from additional healthy and COPD individuals (n=25 and n=7 each for PBL and alveolar macrophages, respectively) and by expanding the pro-inflammatory mediators measured to also include IL-1β, IFNγ, IL-6, IL-8, IL-12p70, and IL-10.

To facilitate this analysis, we used an ELISA-based platform developed by Meso Scale Discovery (MSD), Gaithersburg, Md. USA (www.mesoscale.com) that allows a multiplex format for the analysis of pro-inflammatory cytokines, chemokines, and matrix metalloproteases. This platform relies on proprietary detection and patterned arrays in a 96-well format and that has an extremely large dynamic range enabling detection of these pro-inflammatory mediators from both biological samples (BAL fluid, serum, etc.) and tissue culture supernatant. An MSD plate reader (Sector Imager 2400) was used. These findings demonstrate that human peripheral blood monocytes and alveolar macrophages stimulated by fibronectin promote inflammation via an autocrine thromboxane receptor pathway.

Figure 4:
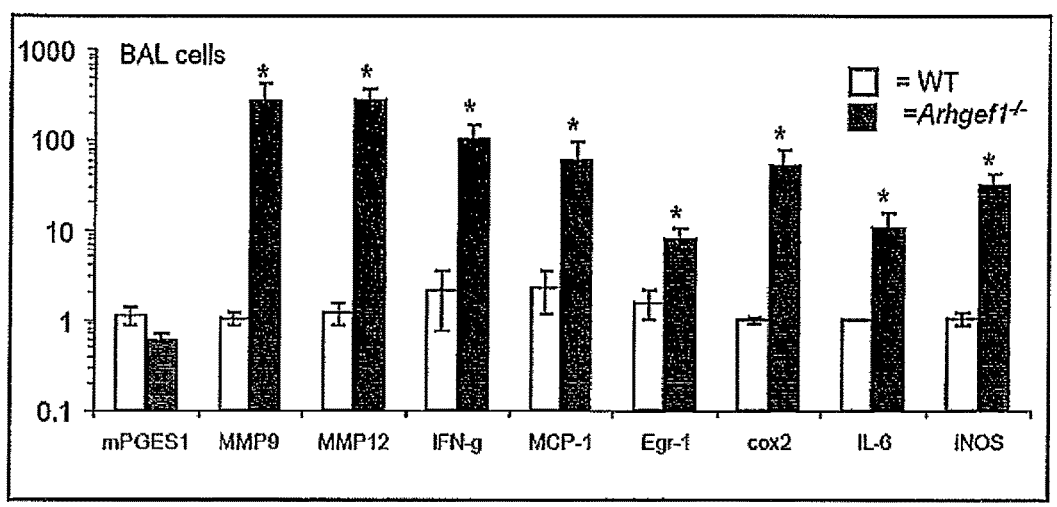
FIG. 4. Expression of several pro-inflammatory mediators is elevated in Arhgef1−/− BAL cells.
Figure 5:
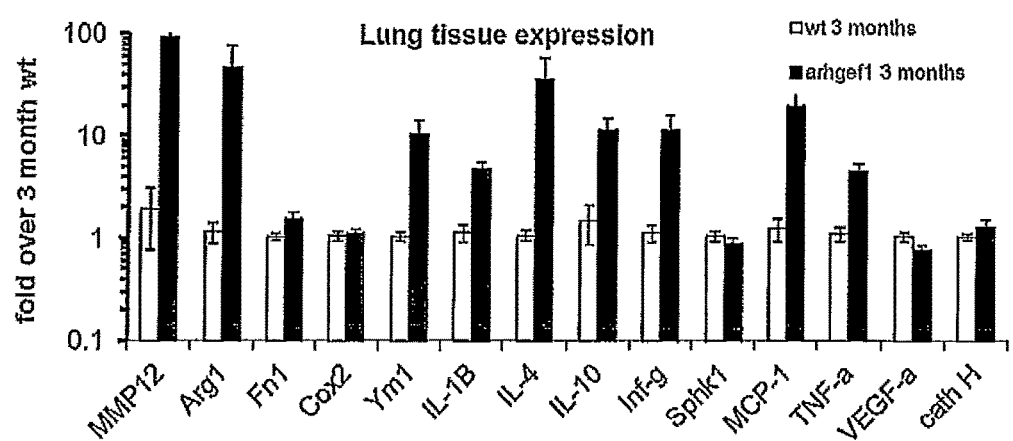
FIG. 5. Expression of several pro-inflammatory mediators is elevated in Arhgef1−/− lung tissue.
Figure 6A:
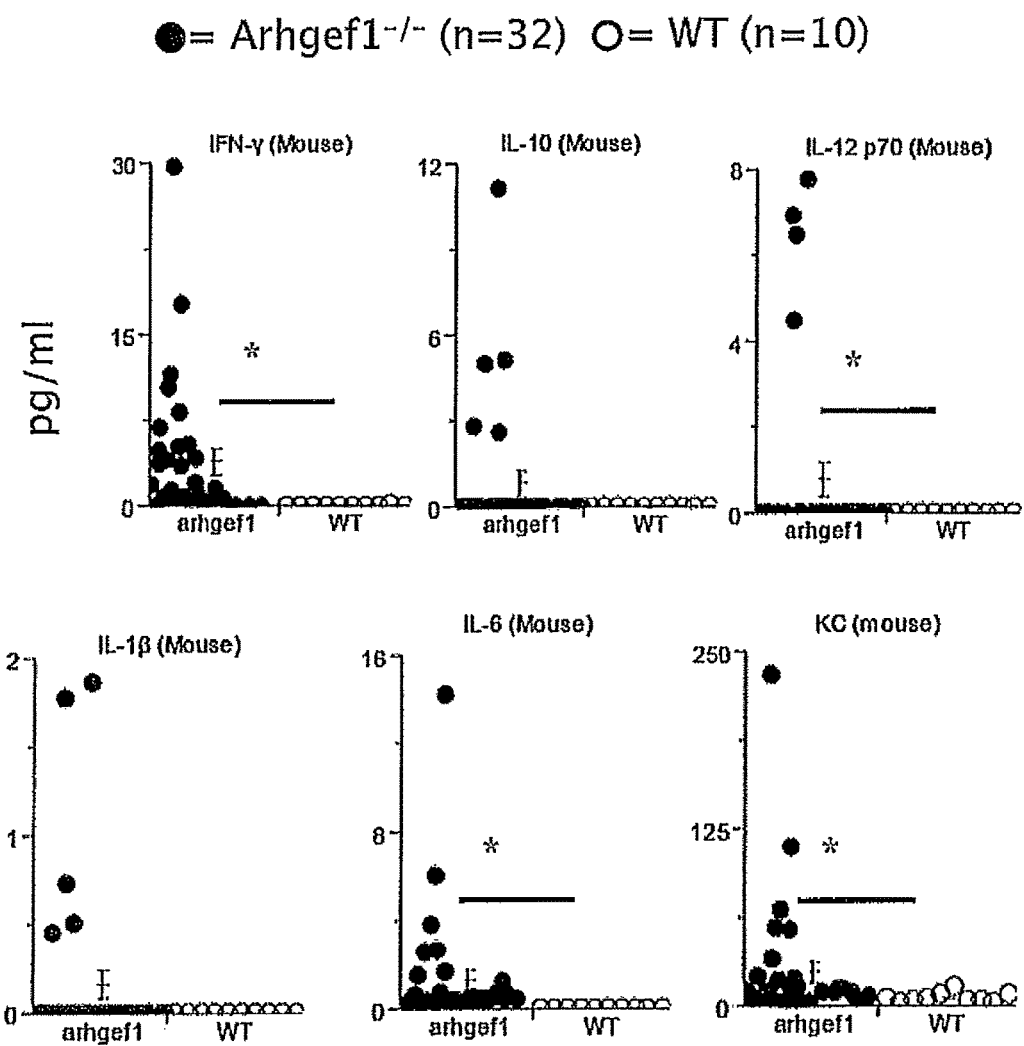
FIG. 6. Panels A and B graphically depict the measurement of pro-inflammatory mediators in bronchoalveolar lavage from naïve wild type (open circles, n=10) and Arhgef1−/− (solid circles, n=32) animals. *=p<0.05 Students two tailed t-test.
Figure 6B:
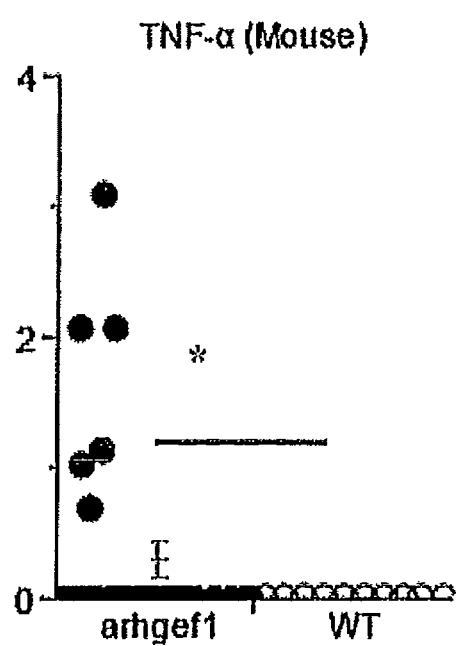
Figure 7:
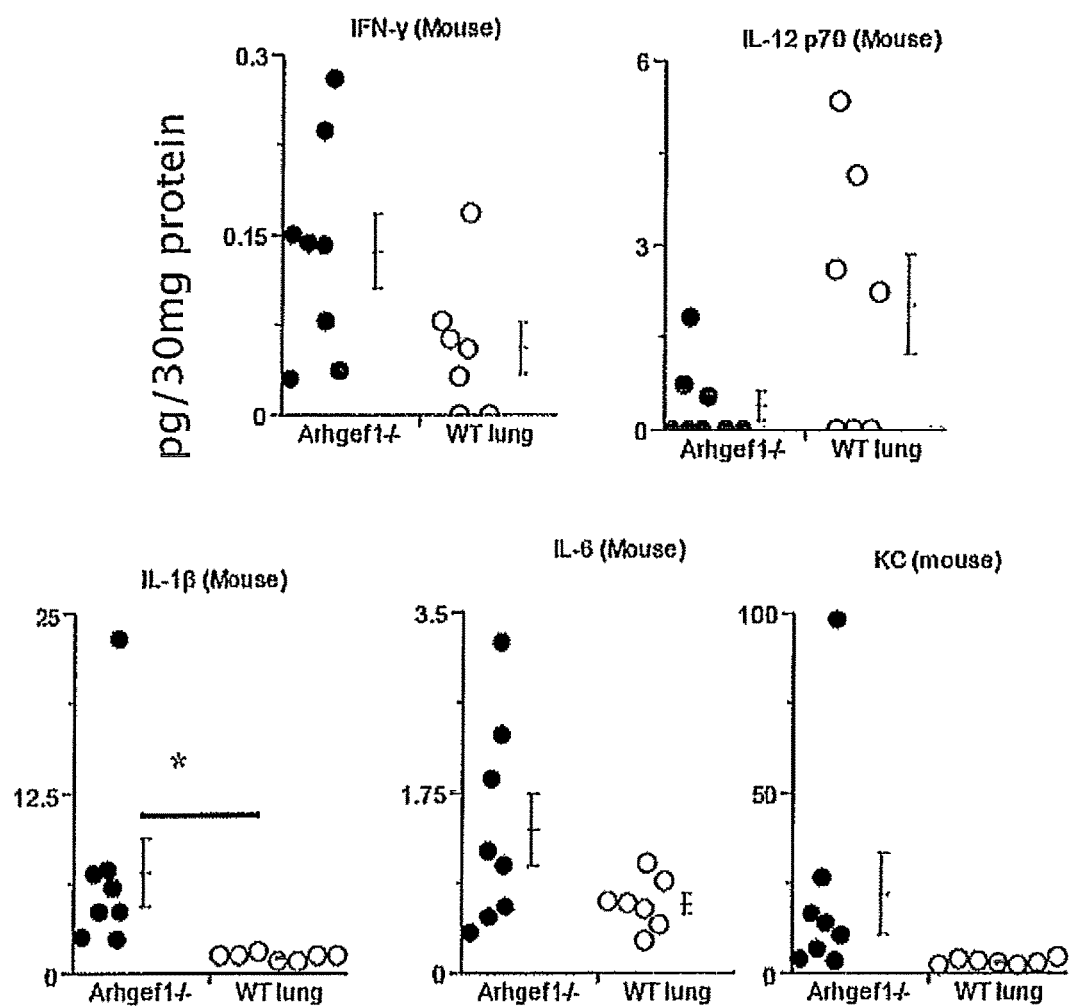
FIG. 7. Measurement of pro-inflammatory mediators in lung tissue from naïve wild type (open circles, n=7) and Arhgef1−/− (solid circles, n=8) animals are graphically depicted. *=p<0.05 Students two tailed t-test. IL-10 and TNF-α measurements were below the level of detection (data not shown).
Figure 8A:
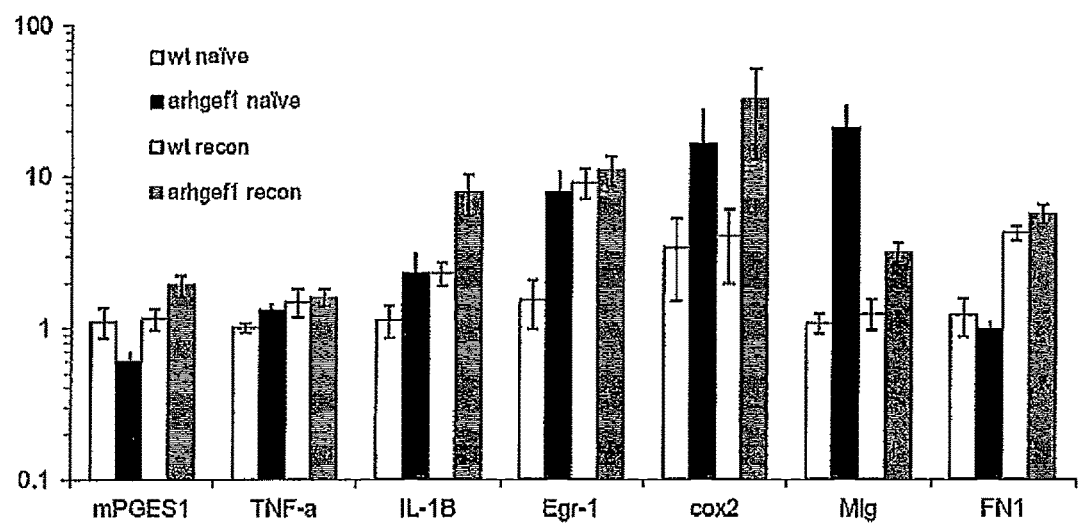
FIG. 8. Panel A graphically depicts that reconstitution of wildtype lungs with Arhgef1−/− peritoneal macrophages recapitulates increased expression of several pro-inflammatory mediators. Each set of bars for the indicated pro-inflammatory mediator, running from left to right, corresponds to wt naïve, arhgef1 naïve, wt recon, and arhgef1 recon. Panel B graphically depicts that the transfer of Arhgef1−/− peritoneal macrophages to the lung of wild type recipient mice results in exaggerated production of pro-inflammatory mediators. Pro-inflammatory mediators were measured by ELISA in BAL supernatant 24 hours after transfer. Either wild type (open circles, n=4) or Arhgef1−/− peritoneal macrophages (solid circles, n=6) were transferred to the airspace of wild type recipient mice. * denotes p<0.05 Students two-tailed t-test.
Figure 8B:
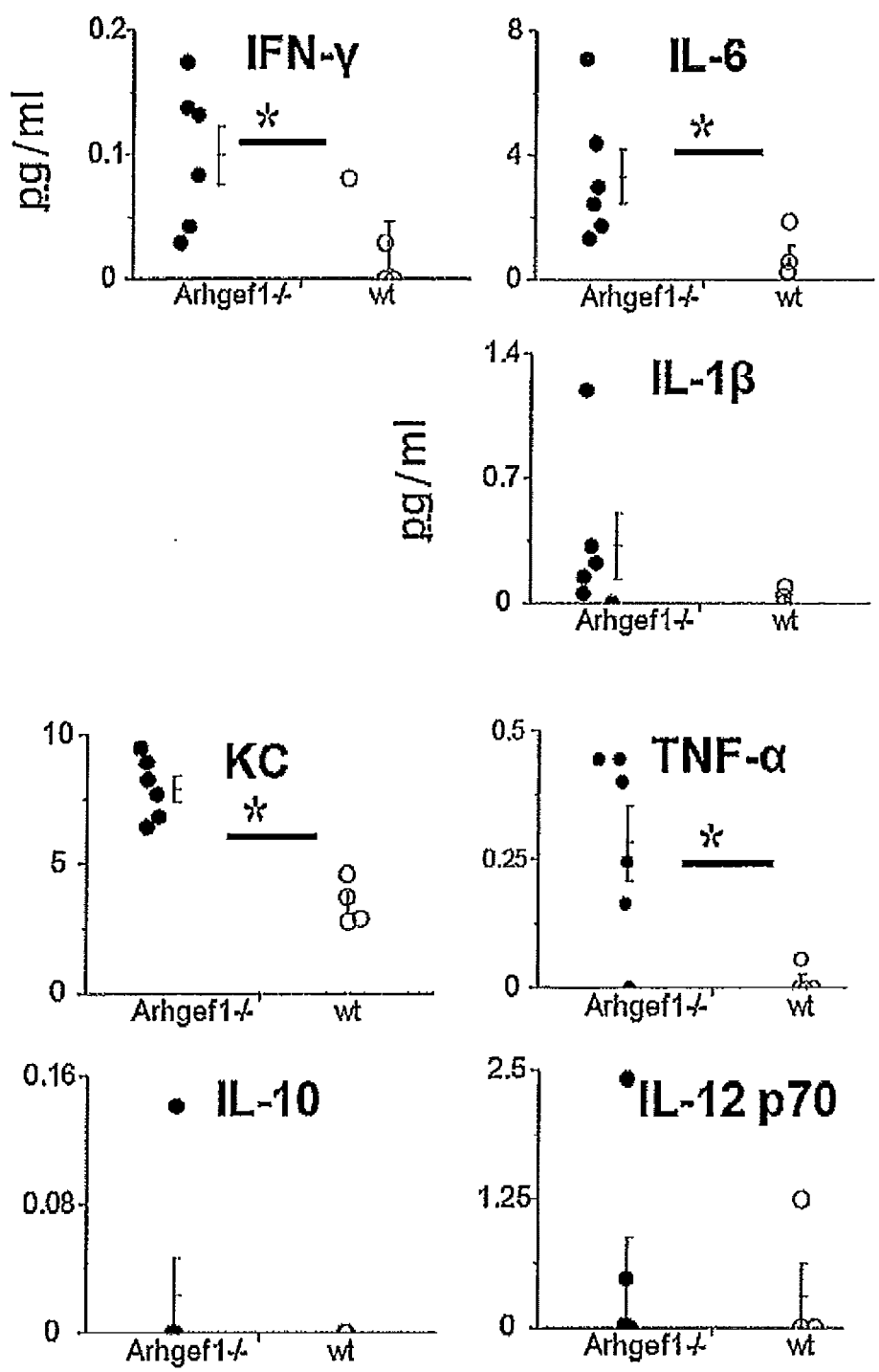

The absence of Arhgef (Arhgef−/− phenotype) results in elevated levels of pro-inflammatory mediators. Experiments summarized in FIG. 4 demonstrate that Arhgef1−/− BAL cells show elevated expression of several pro-inflammatory mediators. Experiments summarized in FIG. 5 demonstrate that Arhgef1−/− lung tissue shows elevated levels of several pro-inflammatory mediators. Experiments summarized in FIG. 6 demonstrate that Arhgef1−/− from bronchoalveolar lavage (BAL) shows elevated levels of several pro-inflammatory mediators. Experiments summarized in FIG. 7 demonstrate that Arhgef1−/− from lung lysate ELISA shows elevated levels of several pro-inflammatory mediators. Experiments summarized in FIG. 8 show that reconstitution of wildtype lungs with Arhgef1−/− peritoneal macrophages recapitulates increased expression of several pro-inflammatory mediators.

Figure 9:
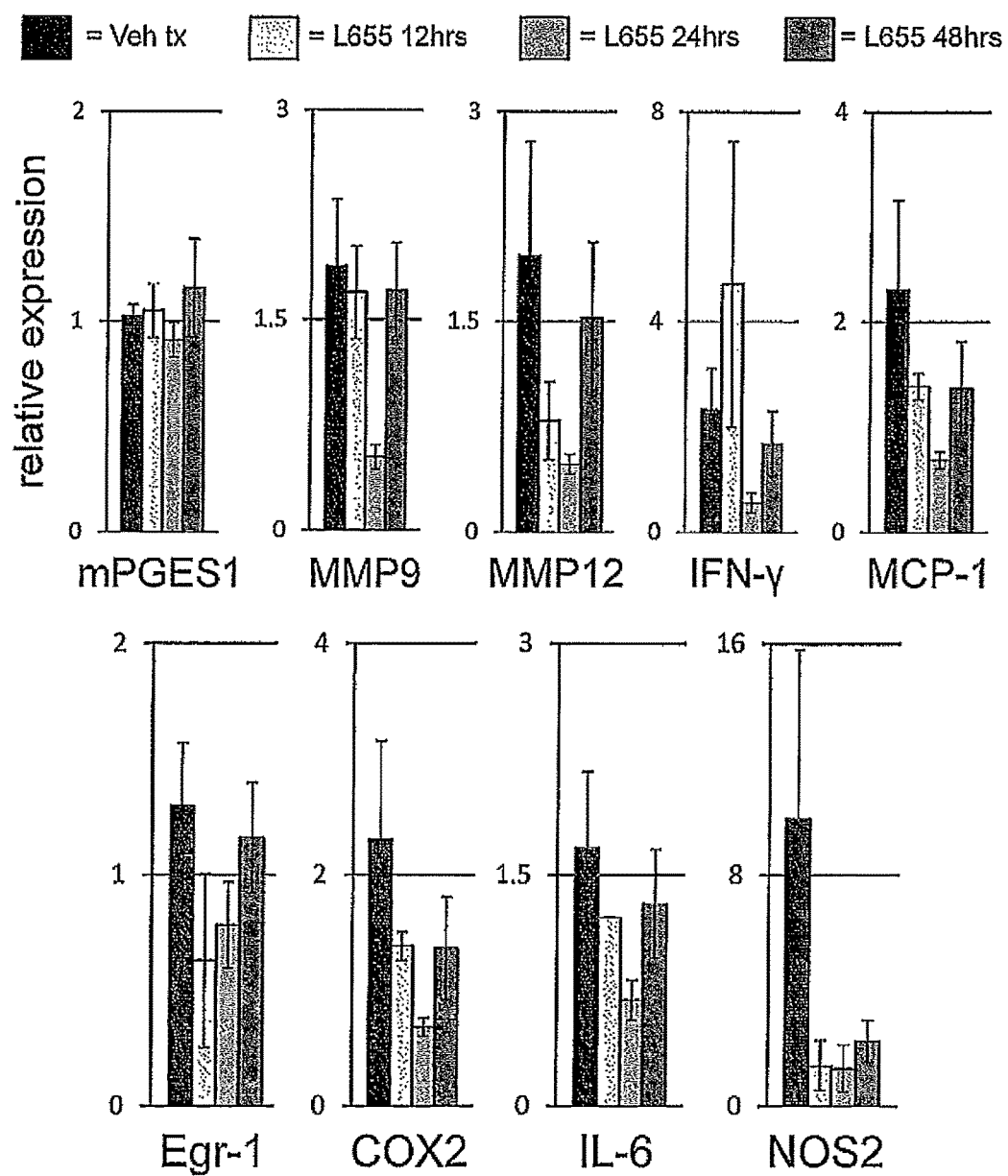
FIG. 9. Arhgef1−/− mice time course of treatment with a single dose of L655 (TP antagonist) RT-PCR of BAL cells that decreases expression of several pro-inflammatory mediators.
Figure 10:
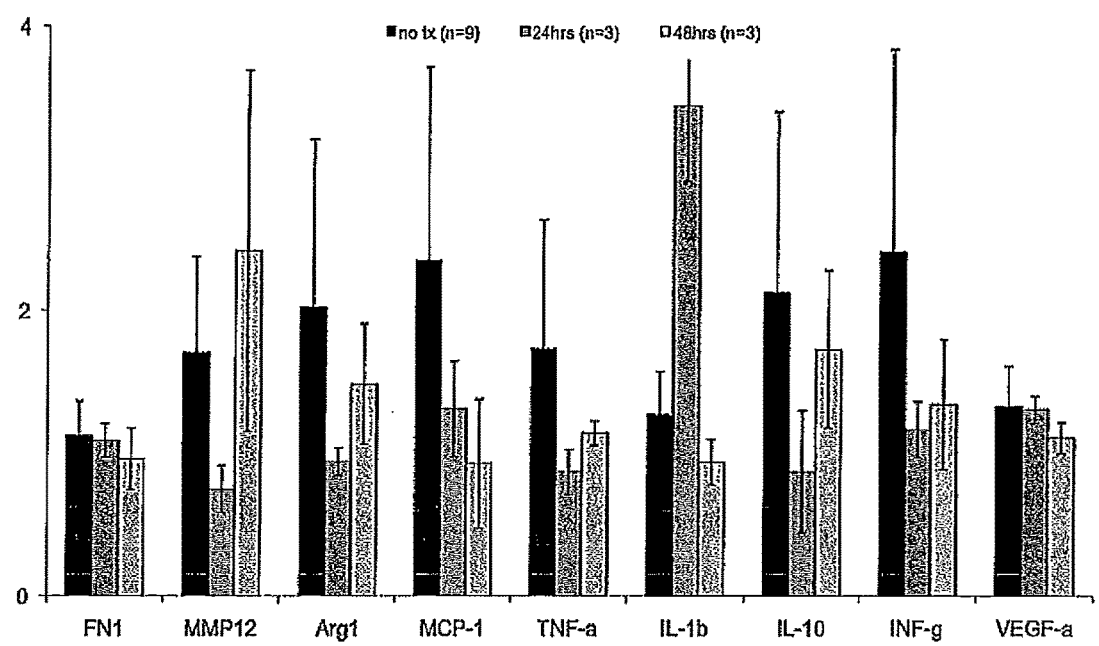
FIG. 10. Arhgef1−/− mice time course of treatment with a single dose of L655 (TP antagonist) RT-PCR of lung tissue that decreases expression of several pro-inflammatory mediators.
Figure 11A:
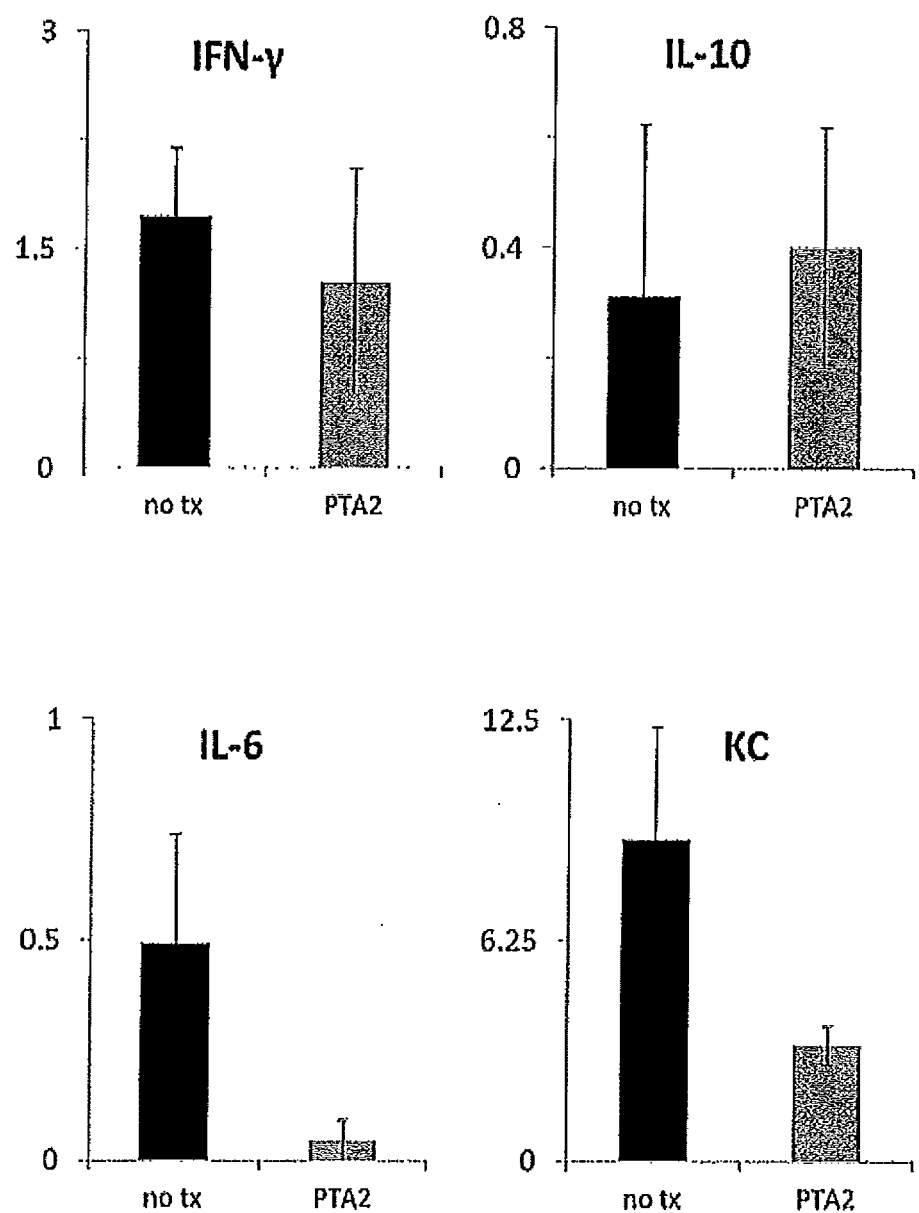
FIG. 11. Panels A and B graphically depict the measurement of BAL pro-inflammatory mediators by ELISA in Arhgef1 deficient animals treated by inhalation of PTA2 or vehicle. As shown, inhalation of PTA2 reduces production of several pro-inflammatory mediators in Arhgef1−/− animals. Pro-inflammatory mediators were measured in BAL supernatant 24 hr after a 1 hr inhalation exposure to either vehicle (black bars on left sides, n=16) or PTA2 (grey bars on right sides, n=3). The data support the experimental data presented in FIGS. 9 and 10.
Figure 11B:
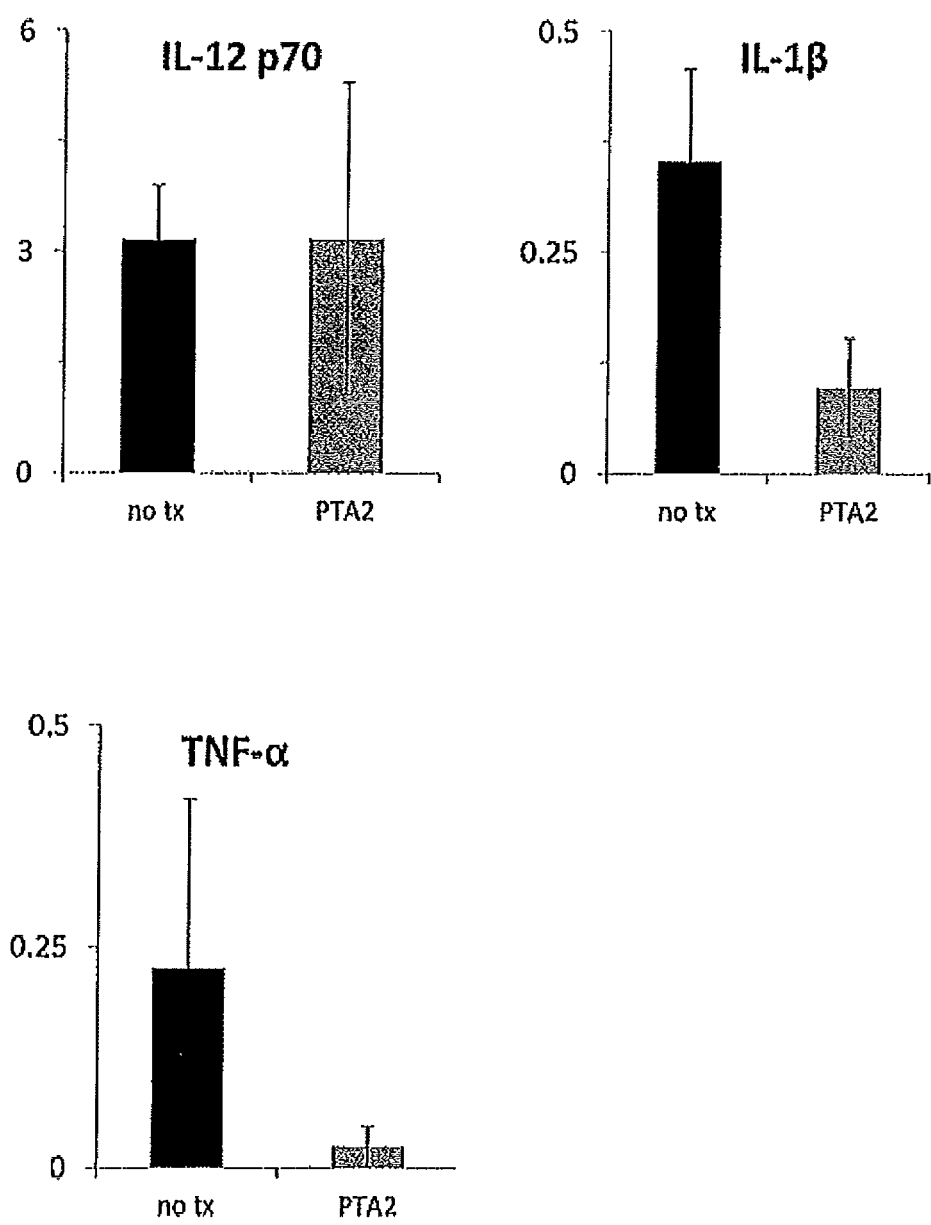

Treatment with a thromboxane receptor antagonist decreases the expression of pro-inflammatory mediators. Experiments summarized in FIG. 9 show an Arhgef1−/− mice time course of treatment with a single dose of L655 (TP antagonist) RT-PCR of BAL cells that decreases expression of several pro-inflammatory mediators. Experiments summarized in FIG. 10 show an Arhgef1−/− mice time course of treatment with a single dose of L655 (TP antagonist) RT-PCR of lung tissue that decreases expression of several pro-inflammatory mediators. FIG. 11A-B shows the results of an MSD analysis of BAL supernatant from Arhgef1-deficient mice after either no treatment or inhalation of Pinane thromboxane A2.

Figure 12:
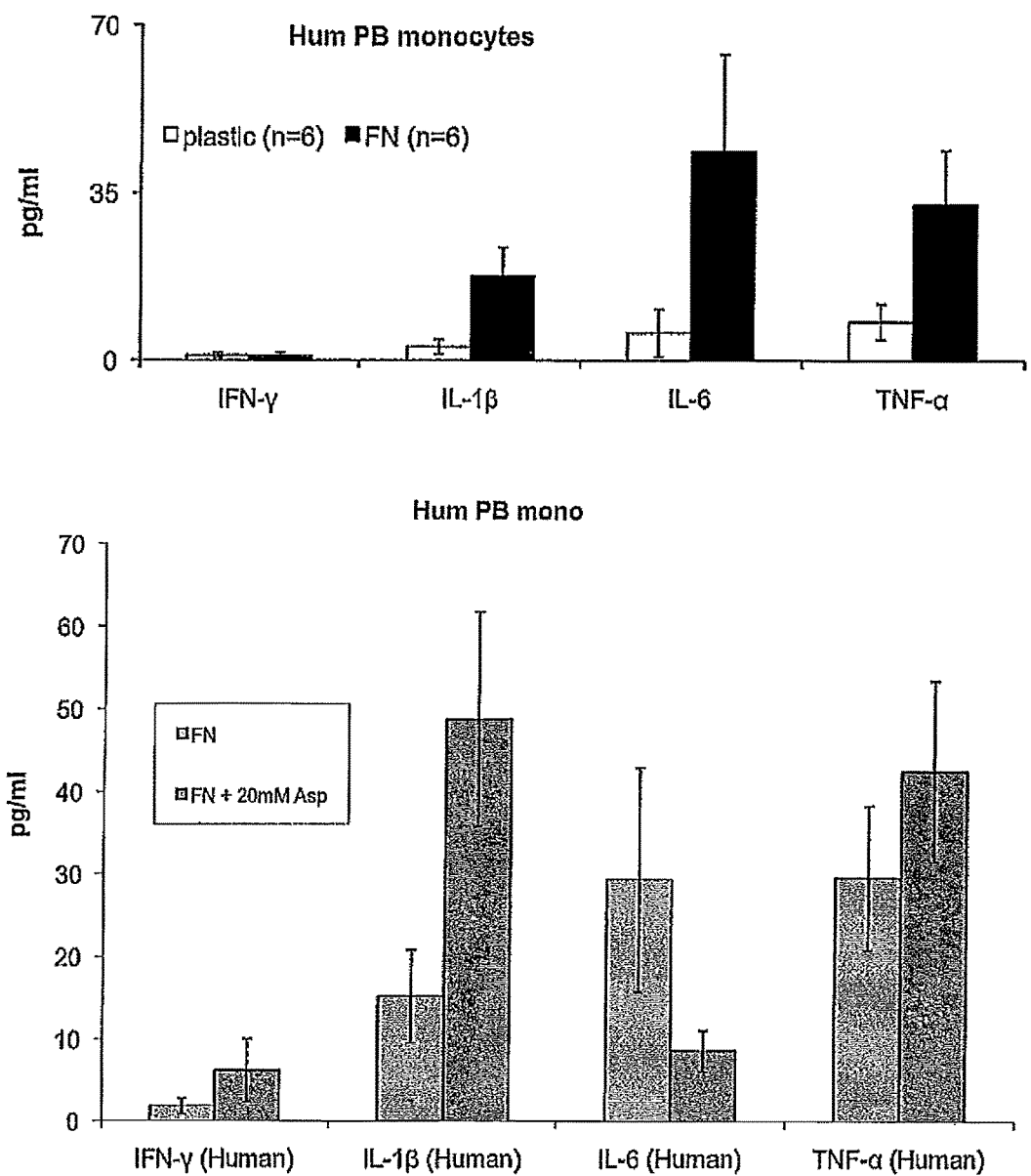
FIG. 12. The top bar graph of FIG. 12 shows that culture of human monocytes on fibronectin (FN) induces several pro-inflammatory mediators as measured by ELISA. The bottom bar graph of FIG. 12 shows that FN induced IL-6 production is reduced by aspirin treatment; left bar of each set is FN and the right bar of each set is FN+20 mM aspirin.

Fibronectin induces the expression of pro-inflammatory mediators, where macrophage adhesion to fibronectin leads to MMP-9 production that is normally inhibited by the Arhgef1 intracellular signaling molecule. Experiments summarized in the top of FIG. 12 show culture of human monocytes on fibronectin (FN) induces several pro-inflammatory mediators as measured by ELISA. The experiments summarized in the bottom of FIG. 12 show that FN induced IL-6 production is reduced by aspirin treatment.

Figure 13:
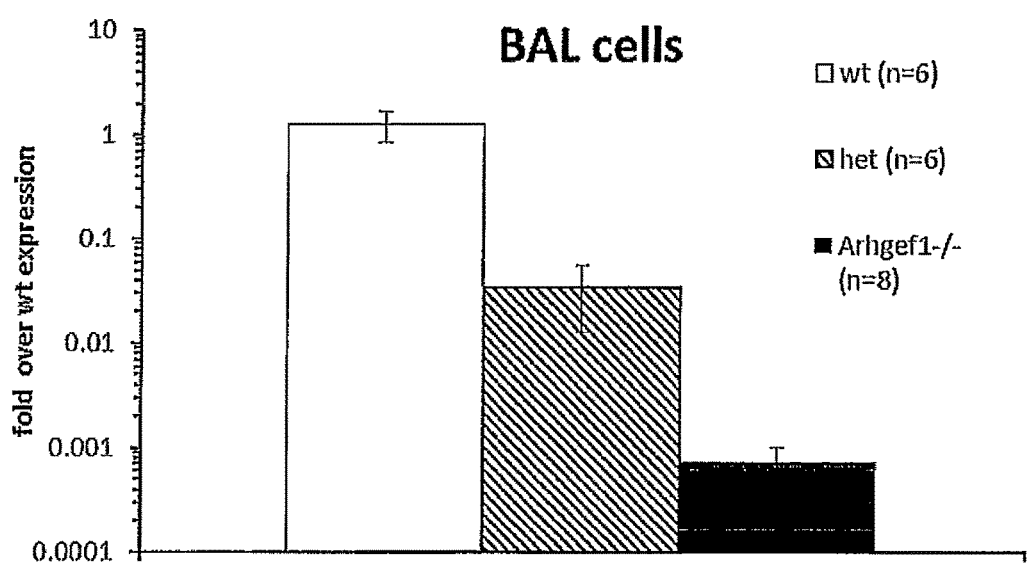
FIG. 13. Depicts RT-PCR data measuring expression of Arhgef1 in murine BAL cells. The set of primers used in this experiment include a targeted exon in Arhgef1−/− mice and provide a low background signal. Expression was normalized to GAPDH and presented as fold over wild type (wt) expression using the delta delta Ct method. The numerical average and plus minus standard error values are: wt=1.26±0.40; het=0.0337±0.021; and Arhgef1−/−=0.00072±0.00028.
Figure 14A:
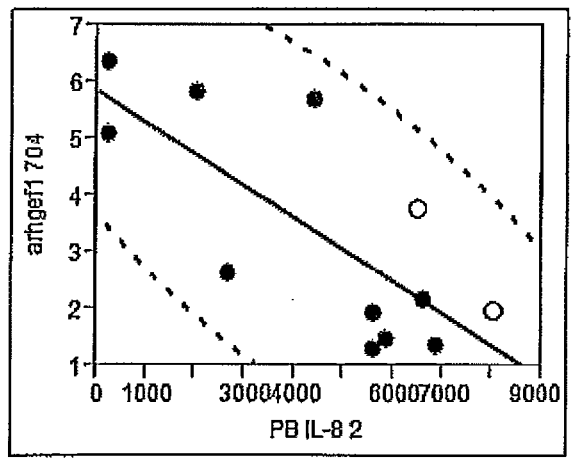
FIG. 14. ARHGEF1 expression is negatively correlated with MCP-1 and IL-8 production by monocytes cultured on fibronectin. Panel A shows data for IL-8 and Panel B shows data for MCP-1. Relative ARHGEF1 expression as measured by RT-PCR is shown on the y axis. ARHGEF1 expression was normalized to GAPDH expression and displayed relative to the lowest expressing individual. MCP-1 and IL-8 production were measured in conditioned media by ELISA and are shown on the x axis. Depicted are the results from monocytes obtained from healthy individuals (open circles n=2) and patients with COPD (solid circles, n=10). A Pearson product moment correlation analysis was performed and a correlation coefficients are shown below each figure. The dotted line denotes bivariate normal ellipse for 95% of the values. The solid line represents the linear fit.
Figure 14A:
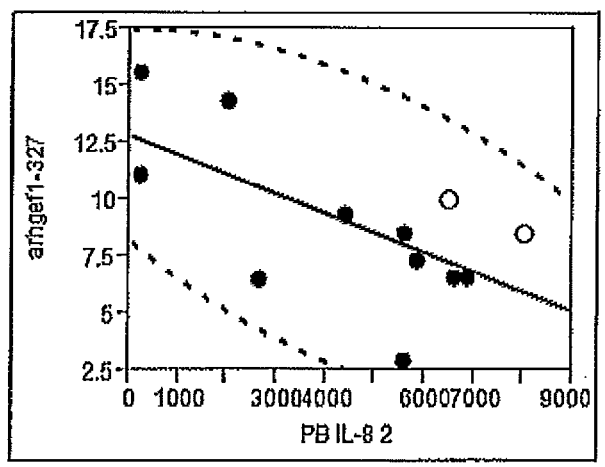
Figure 14B:
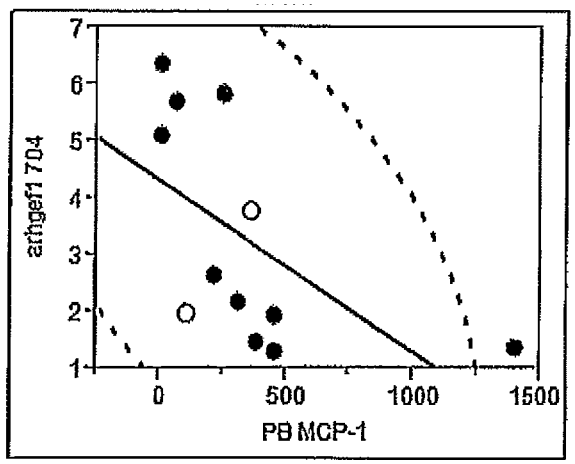
Figure 14B:
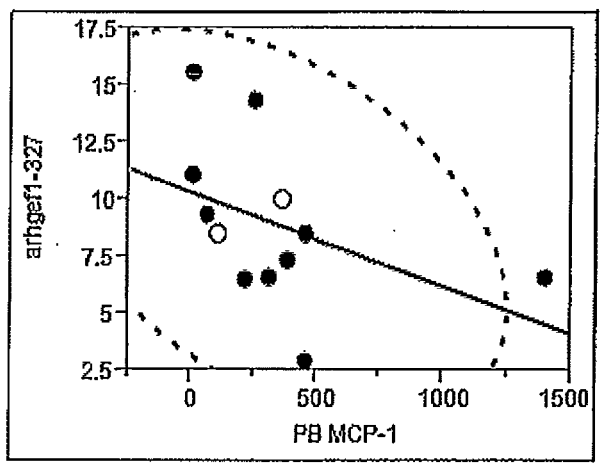

With reference now to FIG. 13, RT-PCR data measuring expression of Arhgef1 in murine BAL cells is shown. The set of primers used in these experiments include a targeted exon in the Arhgef1−/− mice and provide a low background signal. Expression is normalized to GAPDH and presented as fold over wild type (wt) expression using the delta delta Ct method. The average and plus-minus standard error numerical values are: wt=1.26±0.40; het=0.0337±0.021; and Arhgef1−/−=0.00072±0.00028.

ARHGEF1 expression, as shown in FIG. 14, is negatively correlated with MCP-1 and IL-8 production by monocytes cultured on fibronectin. Panel A shows data for IL-8 and Panel B shows data for MCP-1. Relative ARHGEF1 expression as measured by RT-PCR is expressed on the y axis. ARHGEF1 expression was normalized to GAPDH expression and displayed relative to the lowest expressing individual. MCP-1 and IL-8 production was measured in conditioned media by ELISA and is expressed on the x axis. Shown are the results from monocytes obtained from (healthy individuals (open circles n=2) and patients with COPD (solid circles, n=10). A Pearson product moment correlation analysis was performed and a correlation coefficients are shown below each figure. The dotted line denotes bivariate normal ellipse for 95% of the values. The solid line represent the linear fit.

Figure 15:
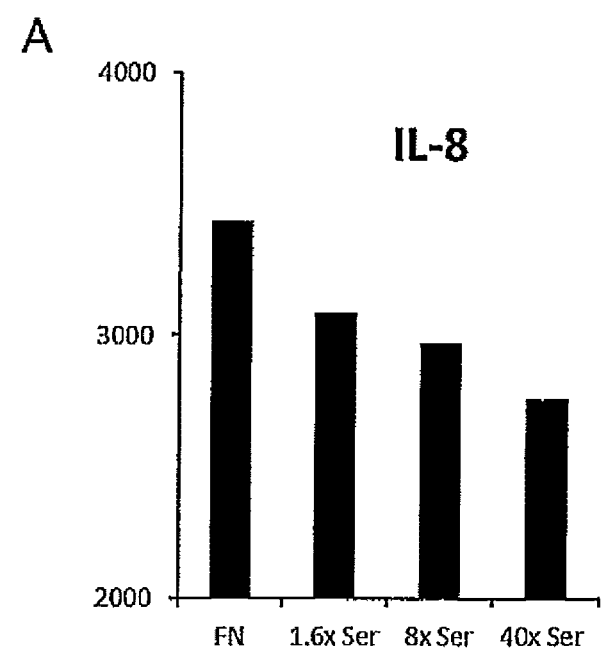
FIG. 15. Two different TP antagonist (PTA2 and Seratrodast) reduce IL-8 production by COPD patient monocytes. Graphically depicted are the results from treating human monocytes cultured on fibronectin with two different TP antagonist. Panel A shows peripheral blood monocytes from a COPD patient cultured on fibronectin that were treated with the following concentrations of Seratrodast: 1.6×=0.448 μM, 8×=2.24 μM, 40×=11.2 μM. Panel B shows peripheral blood monocytes from 3 COPD patients that were cultured on either plastic or fibronectin. Some fibronectin cultured cells were treated with the thromboxane receptor antagonist Pinane Thromboxane (PTA2). For PTA2 treatment, the concentration utilized is 7.5 μM.
Figure 15:
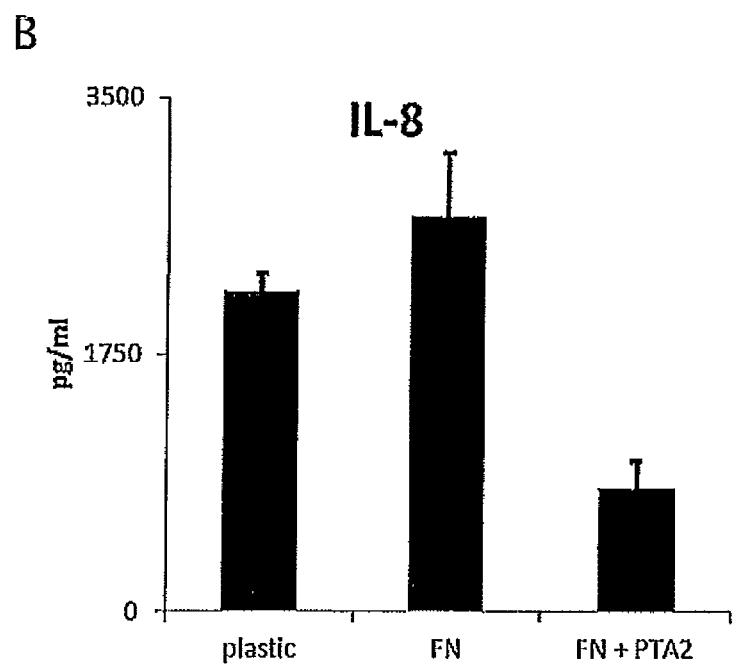

Thromboxane receptor antagonists can inhibit the expression of pro-inflammatory mediators, as shown in FIG. 15. Two different TP antagonists (PTA2 and Seratrodast) reduce IL-8 production by COPD patient monocytes. Treatment with two different TP antagonist reduces IL-8 production by human monocytes cultured on fibronectin, where panel A shows peripheral blood monocytes from a COPD patient cultured on fibronectin that were treated with the following concentrations of Seratrodast: 1.6×=0.448 µM, 8×2.24 µM, 40×=11.2 µM. Panel B shows peripheral blood monocytes from 3 COPD patients that were cultured on either plastic or fibronectin. Some fibronectin cultured cells were treated with the thromboxane receptor antagonist Pinane Thromboxane (PTA2). For PTA2 treatment, the concentration used was 7.5 µM.

Figure 16:
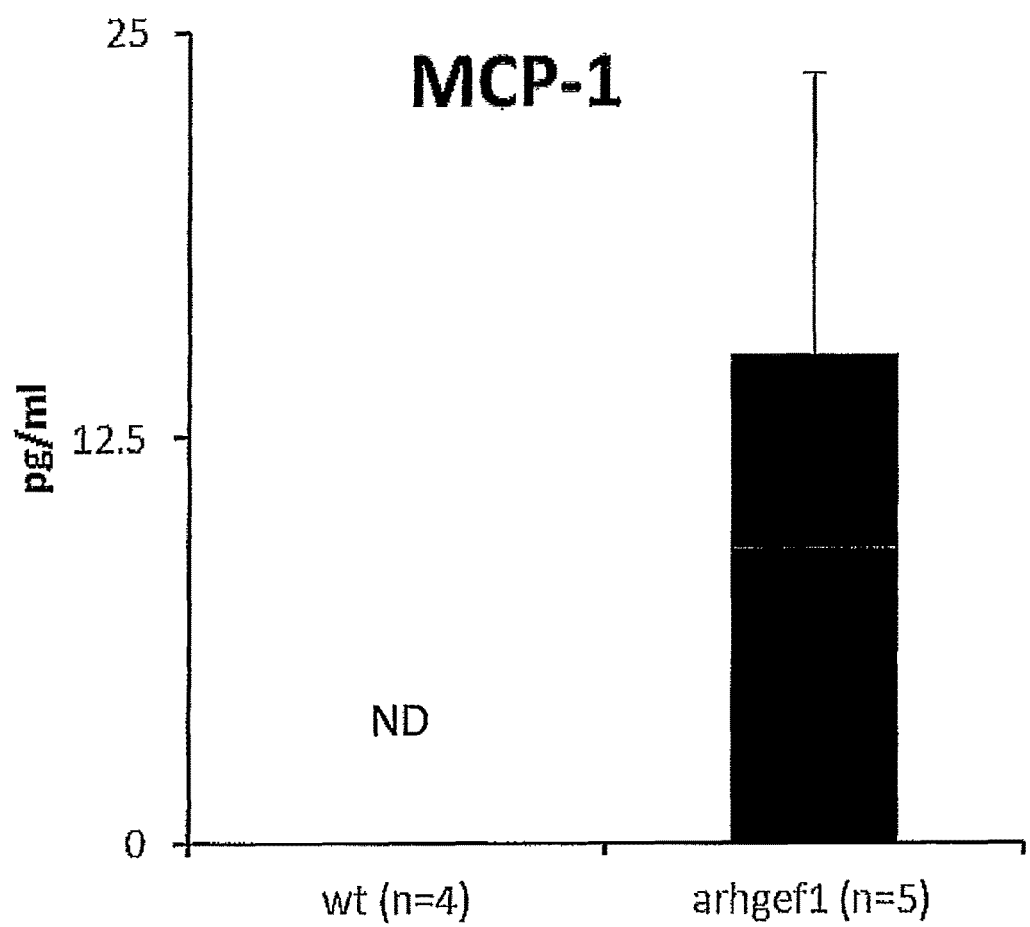
FIG. 16. Given the results of the human studies that establish a relationship between MCP-1 production and ARHGEF1 expression, murine MCP-1 was determined where the bargraph depicts the results of an ELISA measurement of MCP-1 in BAL supernatant from naïve wild type (n=4) and Arhgef1−/− mice (black bar, n=5). ND=all samples were below the level of detection.

Given the results of the human studies that establish a relationship between MCP-1 production and ARHGEF1 expression, additional murine MCP-1 experiments were performed and the data presented in FIG. 16. Panel A is an ELISA measurement of MCP-1 in BAL supernatant from naïve wild type (n=4) and Arhgef1−/− mice (black bar, n=5). ND=all samples were below the level of detection.

Based on the results of these experiments, methods of diagnosing a subject as a pulmonary disease candidate are provided. In one method, leukocyte expression of at least one pro-inflammatory mediator is determined in the subject. The subject is identified as a pulmonary disease candidate when leukocyte expression in the subject of the pro-inflammatory mediator is increased compared to leukocyte expression of the pro-inflammatory mediator in a healthy individual.

In some embodiments, the pro-inflammatory mediator includes a member selected from the group consisting of Matrix Metalloproteinase-9 (MMP-9), Interferon gamma (IFN-γ), Monocyte Chemotactic Protein-1 (MCP-1), Early Growth Response protein 1 (EGR-1), Cyclooxygenase-2 (COX-2), Interleukin-6 (IL-6), inducible Nitric Oxide Synthase (iNOS), Interleukin-8 (IL-8), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Granulocyte-Macrophage Colony-Stimulating Factor (GM-CSF), Macrophage-Derived Chemokine (MDC), Eotaxin, C-Reactive Protein (CRP), Matrix Metalloproteinase-1 (MMP-1), and combinations thereof. In certain embodiments, the pro-inflammatory mediator is selected from the group consisting of Matrix Metalloproteinase-9 (MMP-9), Interferon gamma (IFN-γ), Monocyte Chemotactic Protein-1 (MCP-1), Early Growth Response protein 1 (EGR-1), Cyclooxygenase-2 (COX-2), Interleukin-6 (IL-6), inducible Nitric Oxide Synthase (iNOS), Interleukin-8 (IL-8), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Granulocyte-Macrophage Colony-Stimulating Factor (GM-CSF), Macrophage-Derived Chemokine (MDC), Eotaxin, and combinations thereof. In further embodiments, the pro-inflammatory mediator is selected from the group consisting of Matrix Metalloproteinase-9 (MMP-9), Interferon gamma (IFN-γ), Monocyte Chemotactic Protein-1 (MCP-1), Early Growth Response protein 1 (EGR-1), Cyclooxygenase-2 (COX-2), Interleukin-6 (IL-6), inducible Nitric Oxide Synthase (iNOS), Interleukin-8 (IL-8), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Granulocyte-Macrophage Colony-Stimulating Factor (GM-CSF), Macrophage-Derived Chemokine (MDC), and combinations thereof. In still further embodiments, the pro-inflammatory mediator is selected from the group consisting of Matrix Metalloproteinase-9 (MMP-9), Monocyte Chemotactic Protein-1 (MCP-1), Interleukin-8 (IL-8), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Granulocyte-Macrophage Colony-Stimulating Factor (GM-CSF), Macrophage-Derived Chemokine (MDC), and combinations thereof. In other embodiments, the pro-inflammatory mediator is selected from the group consisting of Matrix Metalloproteinase-9 (MMP-9), Monocyte Chemotactic Protein-1 (MCP-1), Interleukin-8 (IL-8), and combinations thereof.

Leukocyte expression in the present methods can be determined in several ways using various methods known in the art. One example includes the use of ELISA. Leukocyte expression of various pro-inflammatory mediators can also be determined. For example, leukocyte expression in the subject can be determined for a plurality of pro-inflammatory mediators and the subject can be identified as a pulmonary disease candidate when leukocyte expression in the subject of the plurality of pro-inflammatory mediators is increased compared to leukocyte expression of the plurality pro-inflammatory mediators in a healthy individual. In various embodiments, leukocyte expression in the subject can be determined for at least two, three, four, or more pro-inflammatory mediators and the subject can be identified as a pulmonary disease candidate when leukocyte expression in the subject of the at least two, three, four, or more pro-inflammatory mediators is increased compared to leukocyte expression of the at least two, three, four, or more pro-inflammatory mediators in a healthy individual. In certain embodiments, the leukocyte comprises an alveolar macrophage, a monocyte, a monocyte-derived macrophage, or a neutrophil. The pulmonary disease can comprise chronic obstructive pulmonary disease (COPD).

As further established herein, methods of diagnosing a subject as a pulmonary disease candidate and treating the pulmonary disease candidate are provided. One method includes determining leukocyte expression in the subject of at least one pro-inflammatory mediator. The subject is identified as a pulmonary disease candidate when leukocyte expression in the subject of the pro-inflammatory mediator is increased compared to leukocyte expression of the pro-inflammatory mediator in a healthy individual. The pulmonary disease candidate is then treated by administering a therapeutically effective amount of a thromboxane receptor antagonist. Various pro-inflammatory mediators can be used and leukocyte expression in the subject can be determined for a plurality of pro-inflammatory mediators, as described. The leukocyte can likewise comprises an alveolar macrophage, a monocyte, a monocyte-derived macrophage, or a neutrophil and the pulmonary disease can comprise chronic obstructive pulmonary disease (COPD).

Various thromboxane receptor antagonists can be useful in treating the pulmonary disease candidate. Thromboxane receptor activity can be determined and evaluated by various assays and using various methodologies, including commercial kits (e.g., ELISA). Thromboxane receptor antagonists include the following compounds, with suppliers indicated in brackets and common synonyms listed in parentheses: Pinane thromboxane A2 (also known as PTXA2; $PTA_2$; and (1S-(1alpha,2beta(Z),3alpha(1E,3S*),5alpha))-7-(3-(3-Hydroxy-1-octenyl)-6,6-dimethylbicyclo(3.1.1)hept-2-yl)-5-heptenoic acid); L-655,240 (also known as 1-[(4-Chlorophenyl)methyl]-5-fluoro-$\alpha,\alpha$,3-trimethyl-1H-indole-2-propanoic acid); L-670,596 (also known as (−)-6-8-Difluoro-2,3,4,9-tetrahydro-9-[[4-(methylsulfonyl)phenyl]methyl]-1H-carbazole-1-acetic acid); Terutroban [Servier Laboratories] (also known as S-18886; Terutroban salts, including sodium; and 3-[6-[(4-chlorophenyl)sulfonylamino]-2-methyl-5,6,7,8-tetrahydronaphthalen-1-yl]propanoate); PRT061103 [Portola Pharmaceuticals]; Ifetroban [Cumberland Pharmaceuticals] (also known as 3-[2-({(1s,2r,3s)-3-[4-(pentylcarbamoyl)-1,3-oxazol-2-yl]-7-oxabicyclo[2.2.1]hept-2-yl}methyl)phenyl]propanoic acid); Ramatroban [Bayer AG] (also known as BAY-u-3405; 3-[(3R)-3-[(4-fluorophenypsulfonylamino]-1,2,3,4-tetrahydrocarbazol-9-yl]propanoic acid; and (3R)-3-[[(4-Fluorophenypsulfonyl]amino]-1,2,3,4-tetrahydro-9H-carbazole-9-propanoic acid); Seratrodast [Abbott; TAP Pharmaceuticals; Takeda Chemical Industries] (also known as AA-2414; 7-phenyl-7-(2,4,5-trimethyl-3,6-dioxocyclohexa-1,4-dien-1-yl)heptanoic acid; and 7-(3,5,6-Trimethyl-1,4-benzoquinon-2-yl)-7-phenylheptanoic acid); Z-335 [Zeria Pharmaceutical Co., Japan] (also known as Z-335 salts, including sodium; and 2-[2-[[(4-chlorophenyl)sulfonylamino]methyl]-2,3-dihydro-1H-inden-5-yl]acetate); Ridogrel [Janssen Pharmaceuticals] (also known as 5-[(E)-[pyridin-3-yl-[3-(trifluoromethyl)phenyl]methylidene]amino]oxypentanoic acid); Terbogrel [Boehringer Ingelheim] (also known as (E)-6-[3-[(N-tert-butyl-N-cyanocarbamimidoyl)amino]phenyl]-6-pyridin-3-ylhex-5-enoic acid); ICI 185,282 [AstraZeneca] (also known as 5-(Z)-7-(4-o-Hydroxyphenyl-2-trifluoromethyl-1,3 dioxan-cis-5-yl)heptenoic acid); ICI 192,605 (also known as 4-(Z)-6-(2-o-Chlorophenyl-4-o-hydroxyphenyl-1,3-dioxan-cis-5-yl)hexenoic acid); EV-077, EV-075 [Evolva SA]; and SQ 29,548 [Sigma] among others. Various salt, acid, and free base forms of such thromboxane receptor antagonists can be used, including various combinations thereof.

In certain embodiments, the thromboxane receptor antagonist comprises a member selected from the group consisting of Pinane thromboxane A2, L-655,240, L-670,596, Terutroban, PRT061103, Ifetroban, Ramatroban, Seratrodast, Z-335, Ridogrel, Terbogrel, ICI 185,282, ICI 192,605, EV-077, EV-075, SQ 29,548, and combinations thereof. In other embodiments, the thromboxane receptor antagonist comprises a member selected from the group consisting of Pinane thromboxane A2, L-655,240, L-670,596, Terutroban, PRT061103, Seratrodast, EV-077, EV-075, and combinations thereof. In further embodiments, the thromboxane receptor antagonist comprises a member selected from the group consisting of Terutroban, PRT061103, Seratrodast, EV-077, EV-075, and combinations thereof.

The thromboxane receptor antagonist can be administered to a subject in a therapeutically effective amount, which is sufficient to abrogate, substantially inhibit, slow or reverse the progression of a pulmonary disease condition associated with thromboxane receptor activity, to substantially ameliorate clinical symptoms of a such a condition, or to substantially prevent, delay, or reduce the appearance of clinical symptoms of such a condition. The inhibitory amount may be determined directly by measuring the inhibition of thromboxane receptor activity, or, for example, where the desired effect is an effect on an activity downstream of thromboxane receptor activity in a pathway that includes the thromboxane receptor, the inhibition may be measured by measuring a downstream effect, such as measuring MMP-9 production, as described herein.

The amount of the thromboxane receptor antagonist compound that constitutes a therapeutically effective amount can vary depending on such parameters as the compound and its potency, the half-life of the compound in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the compound or that will have an effect on thromboxane receptor activity, or a pathway mediated by thromboxane receptor activity. The therapeutically effective amount can fall in a relatively broad range and can be determined through routine trials. Likewise, the thromboxane receptor antagonist can be administered by one or more parenteral and enteral administration routes. Particular examples of administration routes include oral, intravenous, intraperitoneal, and inhalation by aerosolization.

The present technology also provides methods of selecting a candidate compound for treating a pulmonary disease in a subject. Such a method includes exposing a leukocyte comprising a thromboxane receptor to fibronectin and a compound. Whether the compound inhibits leukocyte expression of at least one pro-inflammatory mediator is determined. The compound is then selected as a candidate compound for treating the pulmonary disease when leukocyte expression of the pro-inflammatory mediator is decreased compared to leukocyte expression of the pro-inflammatory mediator in an absence of the compound.

Methods of selecting a candidate compound for treating a pulmonary disease in a subject can use various pro-inflammatory mediators and leukocyte expression can be determined for a plurality of pro-inflammatory mediators, as described. In some embodiments, the pulmonary disease can be chronic obstructive pulmonary disease (COPD) and/or the leukocyte includes an alveolar macrophage, a monocyte, a monocyte-derived macrophage, or a neutrophil.

Other embodiments of the present technology include methods of treating a pulmonary disease in a subject comprising administering to the subject a therapeutically effective amount of a candidate compound selected according to the methods already described herein.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of diagnosing a subject as a chronic obstructive pulmonary disease candidate and treating the chronic obstructive pulmonary disease candidate comprising:
   determining leukocyte expression in the subject of a plurality of pro-inflammatory mediators, wherein the plurality of pro-inflammatory mediators is selected from the group consisting of Interferon gamma (IFN-γ), Monocyte Chemotactic Protein-1 (MCP-1), Early Growth Response protein 1 (EGR-1), Cyclooxygenase-2 (COX-2), inducible Nitric Oxide Synthase (iNOS), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Macrophage-Derived Chemokine (MDC), Eotaxin-1, C-Reactive Protein (CRP), Matrix Metalloproteinase-1 (MMP-1), and combinations thereof;
   identifying the subject as a chronic obstructive pulmonary disease candidate when leukocyte expression in the subject of the plurality of pro-inflammatory mediators is increased compared to leukocyte expression of the plurality of pro-inflammatory mediators in a healthy individual, wherein the increased expression of the plurality of pro-inflammatory mediators is indicative of an insufficient amount of Arhgef1 to modulate a thromboxane receptor in the leukocyte; and
   treating the chronic obstructive pulmonary disease candidate by administering a therapeutically effective amount of a thromboxane receptor antagonist.

2. The method of claim 1, wherein the pro-inflammatory mediator is selected from the group consisting of Monocyte Chemotactic Protein-1 (MCP-1), Interleukin-12p70 (IL-12p70), Interleukin-2 (IL-2), Eotaxin-3, Interferon gamma-induced Protein 10 (IP-10), Monocyte Chemotactic Protein-4 (MCP-4), Thymus and Activation Regulated Chemokine (TARC), Macrophage-Derived Chemokine (MDC), and combinations thereof.

3. The method of claim 1, wherein the plurality of pro-inflammatory mediators includes Monocyte Chemotactic Protein-1 (MCP-1).

4. The method of claim 1, wherein leukocyte expression in the subject is determined for at least three pro-inflammatory mediators and the subject is identified as a chronic obstructive pulmonary disease candidate when leukocyte expression in the subject of the three pro-inflammatory mediators is increased compared to leukocyte expression of the three pro-inflammatory mediators in a healthy individual.

5. The method of claim 1, wherein the leukocyte is selected from the group consisting of an alveolar macrophage, a monocyte, a monocyte-derived macrophage, and a neutrophil.

6. The method of claim 1, wherein administering the therapeutically effective amount of the thromboxane receptor antagonist comprises a member selected from the group consisting of enteral administration, parenteral administration, inhalation administration, and combinations thereof.

7. The method of claim 1, wherein the thromboxane receptor antagonist comprises a member selected from the group consisting of Pinane thromboxane A2, L-655,240, L-670,596, Terutroban, PRT061103, Ifetroban, Ramatroban, Seratrodast, Z-335, Ridogrel, Terbogrel, ICI 185,282, ICI 192,605, EV-077, EV-075, SQ 29,548, and combinations thereof.

8. The method of claim 1, wherein the thromboxane receptor antagonist comprises a member selected from the group consisting of Pinane thromboxane A2, L-655,240, L-670,596, Terutroban, PRT061103, Seratrodast, EV-077, EV-075, and combinations thereof.

9. The method of claim 1, wherein the thromboxane receptor antagonist comprises a member selected from the group consisting of Terutroban, PRT061103, Seratrodast, EV-077, EV-075, and combinations thereof.

* * * * *